(12) United States Patent
Wei et al.

(10) Patent No.: US 10,591,432 B2
(45) Date of Patent: Mar. 17, 2020

(54) HYDROGEN DETECTION METHOD USING GAS SENSOR HAVING A METAL OXIDE LAYER

(71) Applicant: PANASONIC INTELLECTUAL PROPERTY MANAGEMENT CO., LTD., Osaka (JP)

(72) Inventors: Zhiqiang Wei, Osaka (JP); Kazunari Homma, Kyoto (JP); Satoru Fujii, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 16/525,110

(22) Filed: Jul. 29, 2019

(65) Prior Publication Data
US 2019/0353606 A1 Nov. 21, 2019

Related U.S. Application Data

(62) Division of application No. 15/451,579, filed on Mar. 7, 2017, now Pat. No. 10,408,779.

(30) Foreign Application Priority Data

Mar. 25, 2016 (JP) ................................. 2016-062483

(51) Int. Cl.
*G01N 27/02* (2006.01)
*B60L 58/30* (2019.01)
(Continued)

(52) U.S. Cl.
CPC ............ *G01N 27/125* (2013.01); *B60L 58/30* (2019.02); *G01N 33/005* (2013.01);
(Continued)

(58) Field of Classification Search
CPC ...... G01N 27/125; G01N 27/12; G01N 27/04; G01N 27/02; B60L 58/30; B60L 58/00
(Continued)

(56) References Cited

U.S. PATENT DOCUMENTS 5,362,975 A * 11/1994 von Windheim .... G01N 27/129
204/410
2002/0187075 A1 12/2002 Nadanami et al.
(Continued)

FOREIGN PATENT DOCUMENTS

JP 59-058348 4/1984
JP 60-211347 10/1985
(Continued)

OTHER PUBLICATIONS

Song et al, "AlGaN Schottky diode hydrogen sensor performance at high temperatures with different catalytic metals," Solid State Electronics 45 (2005) 1330-1334. (Year: 2005).
(Continued)

*Primary Examiner* — Christine T Mui
(74) *Attorney, Agent, or Firm* — McDermott Will & Emery LLP

(57) ABSTRACT

A hydrogen detection method using a gas sensor, in which the gas sensor includes a first conductive layer; a second conductive layer including a first region having a first thickness and a second region having a second thickness larger than the first thickness; a metal oxide layer disposed between the first conductive layer and the second conductive layer; and an insulation layer covering the first conductive layer, the second region of the second conductive layer, and the metal oxide layer and not covering the first region of the second conductive layer. The hydrogen detection method includes allowing a gas to come into contact with the first region of the second conductive layer; and detecting a
(Continued)

hydrogen gas contained in the gas by detecting a decrease in resistance between the first conductive layer and the second conductive layer.

1 Claim, 13 Drawing Sheets

(51) Int. Cl.
| | | |
|---|---|---|
| *G01N 27/12* | (2006.01) | |
| *G01N 33/00* | (2006.01) | |
| *H01M 8/04082* | (2016.01) | |
| *H01M 8/0438* | (2016.01) | |
| *H01M 8/04664* | (2016.01) | |

(52) U.S. Cl.
CPC .... *G01N 33/0062* (2013.01); *H01M 8/04201* (2013.01); *H01M 8/04425* (2013.01); *H01M 8/04686* (2013.01); *H01M 2250/20* (2013.01); *Y02T 90/32* (2013.01)

(58) Field of Classification Search
USPC .......................................................... 436/144
See application file for complete search history.

(56) References Cited

U.S. PATENT DOCUMENTS

| | | | |
|---|---|---|---|
| 2013/0071986 A1 | 3/2013 | Deweerd et al. | |
| 2014/0050013 A1 | 2/2014 | Wei et al. | |
| 2017/0276626 A1* | 9/2017 | Wei | H01M 8/04686 |
| 2017/0307557 A1* | 10/2017 | Muraoka | G01N 33/005 |
| 2017/0343507 A1* | 11/2017 | Wei | G01N 27/122 |

FOREIGN PATENT DOCUMENTS

| | | |
|---|---|---|
| JP | 7-128268 | 5/1995 |
| JP | 2007-163253 | 6/2007 |
| JP | 2013-130481 A | 7/2013 |
| WO | 2000/009995 | 2/2000 |
| WO | 2013/080452 A1 | 6/2013 |

OTHER PUBLICATIONS

J.Yu et al., "Hydrogen gas sensing properties of Pt/Ta2O5 Schottky diodes based on Si and SiC substrates", Sensors and Actuators A 172, pp. 9-14, Available online. Feb. 25, 2011.
Non-Final Office Action issued in U.S. Appl. No. 15/451,579, dated Feb. 5, 2019.
Notice of Allowance issued in U.S. Appl. No. 15/451,579, dated Jun. 10, 2019.

* cited by examiner

HYDROGEN DETECTION METHOD USING GAS SENSOR HAVING A METAL OXIDE LAYER

CROSS-REFERENCE OF RELATED APPLICATIONS

This application is a Divisional application of U.S. patent application Ser. No. 15/451,579, filed on Mar. 7, 2017, which claims the benefit of Japanese Application No. 2016-062483, filed on Mar. 25, 2016, the entire disclosures of which Applications are incorporated by reference herein.

BACKGROUND

1. Technical Field

The present disclosure relates to a gas sensor.

2. Description of the Related Art

Japanese Unexamined Patent Application Publication No. 59-58348 has disclosed a gas sensor which detects the presence of a hydrogen gas by the change in resistance. This gas sensor includes a material formed by adding palladium (Pd) and a glass to tantalum pentoxide ($Ta_2O_5$) and platinum (Pt) electrodes sandwiching the material.

In Sensors and Actuators A 172 (2011), p. 9-14, a Pt/$Ta_2O_5$ Schottky diode for hydrogen sensing has been disclosed. In this Schottky diode, a hydrogen molecule is dissociated into hydrogen atoms on the surface of a Pt catalyst.

SUMMARY

In one general aspect, the techniques disclosed here feature a gas sensor which comprises: a first conductive layer; a second conductive layer including a first region having a first thickness and a second region having a second thickness larger than the first thickness; a metal oxide layer disposed between the first conductive layer and the second conductive layer, the metal oxide layer including a bulk region and a local region surrounded by the bulk region, a degree of oxygen deficiency of the local region being higher than that of the bulk region; and an insulation layer covering the first conductive layer, the second region of the second conductive layer, and the metal oxide layer and not covering the first region of the second conductive layer.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
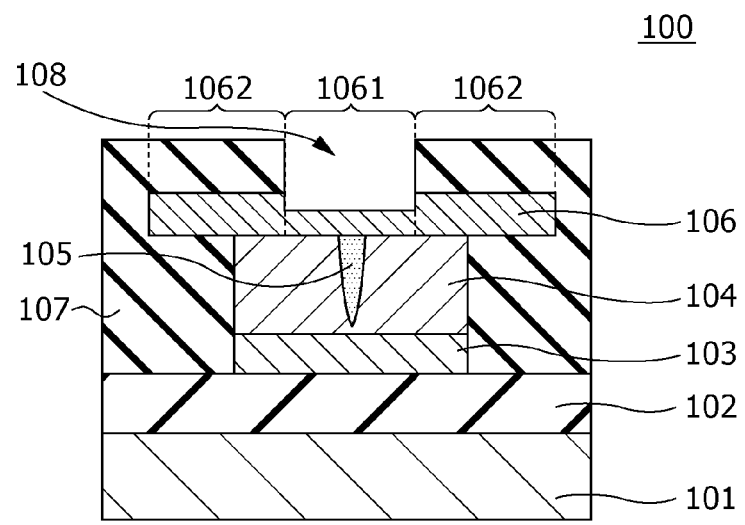
FIG. 1A is a cross-sectional view showing a structural example of a gas sensor according to a first embodiment.

Underlying Knowledge Forming Basis of the Present Disclosure

Through intensive research carried out by the present inventors, the following problems were discovered. In a related gas sensor, in order to improve the sensitivity to detect a gas containing a hydrogen atom, a gas detection element is heated to 100° C. or more. Hence, the power consumption of a related gas sensor is at least approximately 100 mW. Accordingly, when a gas sensor is always used in an ON state, a problem in that the power consumption is remarkably increased may arise.

A gas sensor according to one aspect of the present disclosure is able to rapidly detect a hydrogen-containing gas and is also excellent in electrical power saving.

Hereinafter, embodiments of the present disclosure will be described with reference to the drawings.

Incidentally, in the drawings, an element having substantially the same structure, operation, and effect as that described already will be designated by the same reference numeral, and the description thereof will be omitted. In addition, the numerical value, the material, the composition, the shape, the film forming method, and the like, which will be described below, are shown by way of example in order to particularly explain the embodiment of the present disclosure, and the present disclosure is not limited thereto. In addition, the following connection relationship between the constituent elements to be described below is shown by way of example in order to particularly explain the embodiment of the present disclosure, and the present disclosure is not limited thereto. In addition, among the constituent elements of the following embodiments, the constituent element which is not described in the independent claim representing the most generic concept will be described as an arbitrary constituent element.

First Embodiment

[Structure of Gas Sensor]

A gas sensor according to a first embodiment is a gas sensor having a metal-insulator-metal (MIM) structure in which a resistive film (metal oxide layer) is sandwiched by metal films. This gas sensor uses self-heating and gas sensitivity in a local region formed in the resistive film. Accordingly, the gas sensor can detect a hydrogen-containing gas without performing heating by a heater. In this case, the hydrogen-containing gas is a generic name of a gas formed of molecules each having at least one hydrogen atom, and for example, hydrogen, methane, and an alcohol may be mentioned.

FIG. 1A is a cross-sectional view showing one structural example of a gas sensor 100 according to the first embodiment.

Figure 1B:
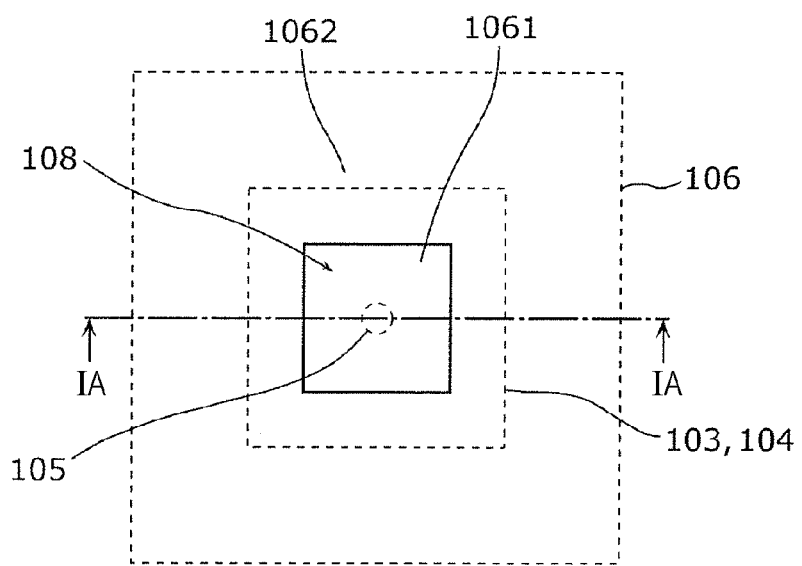
FIG. 1B is a plan view showing a structural example of the gas sensor according to the first embodiment.

FIG. 1B is a plan view showing one structural example of the gas sensor 100 according to the first embodiment. The cross-section of FIG. 1A corresponds to a cross-section viewed in an arrow direction along the section line IA-IA of FIG. 1B.

The gas sensor 100 includes a substrate 101, a first insulation layer 102, a first conductive layer 103, a resistive film 104, a local region 105, a second conductive layer 106, and a second insulation layer 107. In this case, the resistive film 104 is one example of a metal oxide layer.

The first insulation layer 102 is disposed on the substrate 101, and the first conductive layer 103 is disposed on the first insulation layer 102. The second insulation layer 107 is disposed on the first insulation layer 102 and the second conductive layer 106.

The first conductive layer 103 and the second conductive layer 106 are disposed so that the respective principal surfaces thereof face each other above the first insulation layer 102. The resistive film 104 is disposed in contact with the principal surface of the first conductive layer 103 and the principal surface of the second conductive layer 106.

In the second insulation layer 107, an opening 108 is provided so that the second conductive layer 106 is in contact with a gas to be inspected. In other words, the second insulation layer 107 covers the first conductive layer 103, the second conductive layer 106, and the resistive film 104. However, at least a part of the upper surface (the other surface facing the principal surface described above) of the second conductive layer 106 is exposed without being covered with the second insulation layer 107.

The thickness of an exposed first portion 1061 of the second conductive layer 106 is smaller than the thickness of a second portion 1062 of the second conductive layer 106 covered with the second insulation layer 107. The second conductive layer 106 is a single layer in which the thickness of the first portion 1061 and the thickness of the second portion 1062 are different from each other and may be formed, for example, by removing a part of a flat plate having the thickness of the second portion 1062 so as to form the first portion 1061.

The resistive film 104 is provided between the first conductive layer 103 and the second conductive layer 106. The resistance of the resistive film 104 is changed in accordance with an electrical signal applied between the first conductive layer 103 and the second conductive layer 106. In particular, the resistive state of the resistive film 104 is reversibly changed between a high resistive state and a low resistive state in accordance with a voltage (potential difference) applied between the first conductive layer 103 and the second conductive layer 106. In addition, the resistive state of the resistive film 104 is changed from a high resistive state to a low resistive state in response to a hydrogen-containing gas to be brought into contact with the second conductive layer 106.

The local region 105 is formed from the same metal oxide as that of the resistive film 104. The local region 105 is disposed in the resistive film 104 so as to be in contact with the second conductive layer 106 and is not in contact with the first conductive layer 103. The degree of oxygen deficiency of the local region 105 is high as compared to the degree of oxygen deficiency of the periphery thereof (that is, a bulk region of the resistive film 104). The degree of oxygen deficiency of the local region 105 is reversibly changed in accordance with an electrical signal to be applied between the first conductive layer 103 and the second conductive layer 106. In addition, the local region 105 is changed from the state of a low degree of oxygen deficiency to the state of a high degree of oxygen deficiency in response to a hydrogen-containing gas to be brought into contact with the second conductive layer 106.

The local region 105 is a minute region in which a filament (conductive path) formed from oxygen defect sites is assumed to be generated and lost. It is believed that the change in resistance of the resistive film 104 occurs when the filament is generated or lost by an oxidation-reduction reaction performed in the local region 105.

In addition, in the present disclosure, the "degree of oxygen deficiency" of a metal oxide indicates the rate of a deficient amount of oxygen of the metal oxide to the amount of oxygen of an oxide having a stoichiometric composition formed from the same elements as those of the metal oxide (in this case, the deficient amount of oxygen is obtained by deducting the amount of oxygen of the metal oxide from the amount of oxygen of a metal oxide having a stoichiometric composition). If there are a plurality of metal oxides having stoichiometric compositions formed from the same elements as those of the metal oxide, the degree of oxygen deficiency of the metal oxide is defined by one metal oxide having the highest resistance among the metal oxides having stoichiometric compositions. A metal oxide having a stoichiometric composition is stabler than a metal oxide having another composition and has a higher resistance than that thereof.

For example, when the metal is tantalum (Ta), since an oxide having a stoichiometric composition by the above definition is $Ta_2O_5$, it can be represented by $TaO_{2.5}$. The degree of oxygen deficiency of $TaO_{2.5}$ is 0%, and the degree of oxygen deficiency of $TaO_{1.5}$ is (2.5−1.5)/2.5=40%. In addition, a metal oxide having an excess amount of oxygen has a negative degree of oxygen deficiency. In addition, in the present disclosure, unless otherwise particularly noted, the degree of oxygen deficiency can be represented by a positive value, 0, or a negative value.

An oxide having a low degree of oxygen deficiency has a high resistance since being closer to an oxide having a stoichiometric composition, and an oxide having a high degree of oxygen deficiency has a low resistance since being closer to a metal forming the oxide.

An "oxygen content" is the rate of the number of oxygen atoms to the total number of atoms. For example, the oxygen content of $Ta_2O_5$ is a rate (O/(Ta+O)) of the number of oxygen atoms to the total number of atoms and is 71.4 atomic percent. Hence, the oxygen content of an oxygen deficient-type tantalum oxide is larger than 0 and smaller than 71.4 atomic percent.

The local region 105 is formed in the resistive film 104 by applying an initial break voltage between the first conductive layer 103 and the second conductive layer 106. In other words, the initial break voltage is a voltage to be applied between the first conductive layer 103 and the second conductive layer 106 in order to form the local region 105. The absolute value of the initial break voltage may be higher than a writing voltage. The writing voltage is a voltage to be applied between the first conductive layer 103 and the second conductive layer 106 so that the resistive film 104 is reversibly changed between a high resistive state and a low resistive state. The absolute value of the initial break voltage may be lower than the writing voltage. In this case, the initial break voltage may be repeatedly applied or may be continuously applied for a predetermined time. By application of the initial break voltage, as shown in FIG. 1A, the local region 105 in contact with the second conductive layer 106 and not in contact with the first conductive layer 103 is formed.

The local region 105 is a minute region corresponding to filaments required for a current flow. The formation of filaments in the local region 105 may be explained using a percolation model.

The percolation model is a model based on the theory in which a random distribution of oxygen defect sites in the local region 105 is assumed, and when the density of the oxygen defects sites or the like exceeds a predetermined threshold value, the probability of forming linkage between the oxygen defect sites is increased.

According to the percolation model, the filament is formed when a plurality of oxygen defect sites in the local region 105 are linked with each other, and the change in resistance of the resistive film 104 occurs when the oxygen defect sites in the local region 105 are generated and lost.

In this embodiment, the "oxygen defect" indicates that oxygen in this metal oxide is deficient from the stoichiometric composition thereof. The "density of oxygen defect sites" corresponds to the degree of oxygen deficiency. That is, when the degree of oxygen deficiency is increased, the density of oxygen defect sites is also increased.

The local region 105 may be formed only at one place of the resistive film 104 of the gas sensor 100. The number of local regions 105 formed in the resistive film 104 may be confirmed, for example, by an electron beam absorbed current (EBAC) analysis.

When the local region 105 is present in the resistive film 104, by application of a voltage between the first conductive layer 103 and the second conductive layer 106, a current in the resistive film 104 flows concentratedly through the local region 105.

The size of the local region 105 is small. Hence, for example, the local region 105 generates heat by a current of approximately several tens of microamperes which flows when the resistance is read, and by this heat generation, a significant increase in temperature occurs. When a current of approximately several tens of microamperes flows, the power consumption thereby is less than 0.1 mW.

The second conductive layer 106 is formed of a metal (such as Pt) having a catalyst function, and the local region 105 is in contact with the second conductive layer 106. By the structure as described above, the second conductive layer 106 is heated by the heat generation in the local region 105, and a hydrogen atom is efficiently dissociated from a hydrogen-containing gas.

When a hydrogen-containing gas is contained in a gas to be inspected, at the second conductive layer 106, a hydrogen atom is dissociated from a hydrogen-containing gas, the hydrogen atom thus dissociated is bonded to an oxygen atom in the local region 105, and as a result, the resistance of the local region 105 is decreased.

As described above, the gas sensor 100 has a characteristic in which the resistance between the first conductive layer 103 and the second conductive layer 106 is decreased when the second conductive layer 106 is in contact with a hydrogen-containing gas. By this characteristic described above, when a gas to be inspected is brought into contact with the second conductive layer 106, by detecting the decrease in resistance between the first conductive layer 103 and the second conductive layer 106, a hydrogen-containing gas contained in the gas can be detected.

In addition, even if the local region 105 is placed in any one of a high resistive state and a low resistive state, when a hydrogen-containing gas is brought into contact with the second conductive layer 106, the resistance is further decreased. Hence, regardless of whether the local region 105 is placed in any one of a high resistive state and a low resistive state, the gas sensor 100 can detect hydrogen. However, in order to more clearly detect the decrease in resistance, a gas sensor 100 in which the local region 105 is set in an high resistive state in advance may also be used.

Hereinafter, details of the gas sensor 100 configured to obtain a stable resistance change characteristic will be described.

The resistive film 104 is formed of an oxygen deficient-type metal oxide. A mother metal of the metal oxide may be at least one selected from the group consisting of transition metals, such as tantalum (Ta), hafnium (Hf), titanium (Ti), zirconium (Zr), niobium (Nb), tungsten (W), nickel (Ni), and iron (Fe), and aluminum (Al). Since a transition metal is able to have a plurality of oxidized states, different resistive states can be realized by an oxidation-reduction reaction. In this case, the oxygen deficient-type metal oxide is a metal oxide having a high degree of oxygen deficiency as compared to a metal oxide which contains the same metal as that thereof and which has a stoichiometric composition. A metal oxide having a stoichiometric composition is a typical insulating material, and on the other hand, an oxygen deficient-type metal oxide typically shows semiconductor characteristics. When an oxygen deficient-type metal oxide is used for the resistive film 104, the gas sensor 100 is able to realize a stable resistance change operation with good reproducibility.

For example, when a hafnium oxide is used as a metal oxide forming the resistive film 104, and the composition thereof is represented by $HfO_x$, if x is 1.6 or more, the resistance of the resistive film 104 can be stably changed. In this case, the thickness of the hafnium oxide may be set to 3 to 4 nm.

In addition, when a zirconium oxide is used as a metal oxide forming the resistive film 104, and the composition thereof is represented by $ZrO_x$, if x is 1.4 or more, the resistance of the resistive film 104 can be stably changed. In this case, the thickness of the zirconium oxide may be set to 1 to 5 nm.

In addition, when a tantalum oxide is used as a metal oxide forming the resistive film 104, and the composition thereof is represented by $TaO_x$, if x is 2.1 or more, the resistance of the resistive film 104 can be stably changed.

The compositions of the above respective metal oxide layers each can be measured using a Rutherford backscattering method.

As a material of the first conductive layer 103 and the second conductive layer 106, for example, one selected from the group consisting of platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), and titanium aluminum nitride (TiAlN) may be used.

In particular, the second conductive layer 106 may be formed, for example, of a material having a catalyst function, such as platinum (Pt), iridium (Ir), or palladium (Pd), which dissociates a hydrogen atom from a gas molecule containing a hydrogen atom. In addition, the first conductive layer 103 may be formed, for example, of a material having a low standard electrode potential, such as tungsten (W), nickel (Ni), tantalum (Ta), titanium (Ti), aluminum (Al), tantalum nitride (TaN), or titanium nitride (TiN), as compared to that of a metal forming the metal oxide. As the standard electrode potential of a metal is higher, the metal is more unlikely to be oxidized.

In addition, as the substrate 101, for example, although a silicon single crystal substrate or a semiconductor substrate may be used, the substrate 101 is not limited thereto. Since the resistive film 104 can be formed at a relatively low substrate temperature, for example, the resistive film 104 may be formed on a resin material or the like.

In addition, the gas sensor 100 may further include, for example, a fixed resistance, a transistor, or a diode, as a load element electrically connected to the resistive film 104.

Modified Example 1

Figure 2:
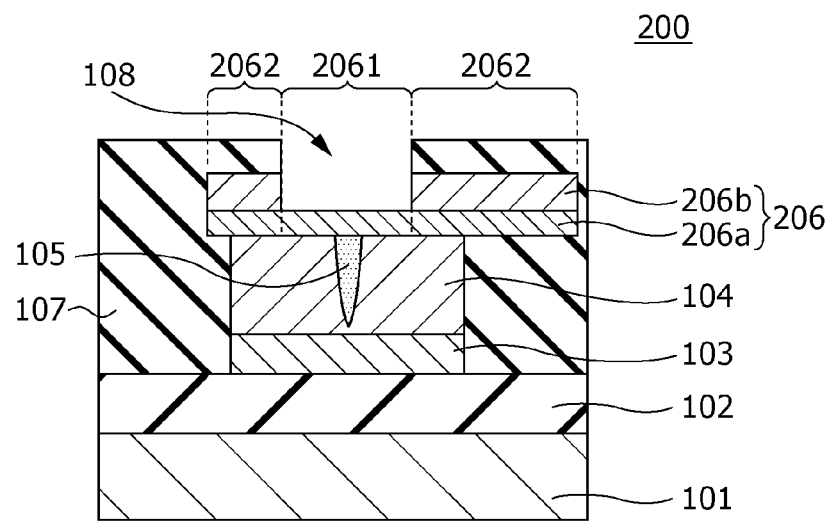
FIG. 2 is a cross-sectional view showing the structure of a gas sensor according to a modified example 1 of the first embodiment.

FIG. 2 is a cross-sectional view showing one structural example of a gas sensor 200 according to a modified example 1 of the first embodiment. Hereinafter, among constituent elements of the gas sensor 200, the same constituent element as that of the gas sensor 100 of the first embodiment is designated by the same reference numeral, the description thereof is omitted, and a different point will only be described.

Since a second conductive layer 206 is a laminate including a lower layer 206a in contact with the resistive film 104 and an upper layer 206b disposed on the lower layer 206a, the gas sensor 200 is different from the gas sensor 100 of the first embodiment. The other constituent elements of the gas sensor 200 are the same as those of the gas sensor 100.

The lower layer 206a is provided to have an approximately flat shape with a thickness of an exposed first portion 2061. The upper layer 206b is provided, other than the first portion 2061, on the lower layer 206a in a second portion 2062 of the second conductive layer 206 which is covered with the insulation layer 107.

Accordingly, the lower layer 206a is exposed at the first portion 2061 through the opening 108. The thickness of the first portion 2061 at which the second conductive layer 206 is exposed is smaller than the thickness of the second portion 2062 of the second conductive layer 206 covered with the insulation layer 107.

In this case, the lower layer 206a is formed of a material, such as platinum or palladium, having a catalyst function. The upper layer 206b is formed of an conductive material, such as titanium nitride (TiN).

By the structure as described above, the lower layer 206a having a catalyst function can be designed to have a small thickness (such as 15 nm). When titanium nitride used as the upper layer 206b is etched to form the opening 108, platinum or palladium used as the lower layer 206a works as an etching stopper. As a result, by the lower layer 206a having a catalyst function, the time for detecting hydrogen can be accurately designed.

Modified Example 2

Figure 3:
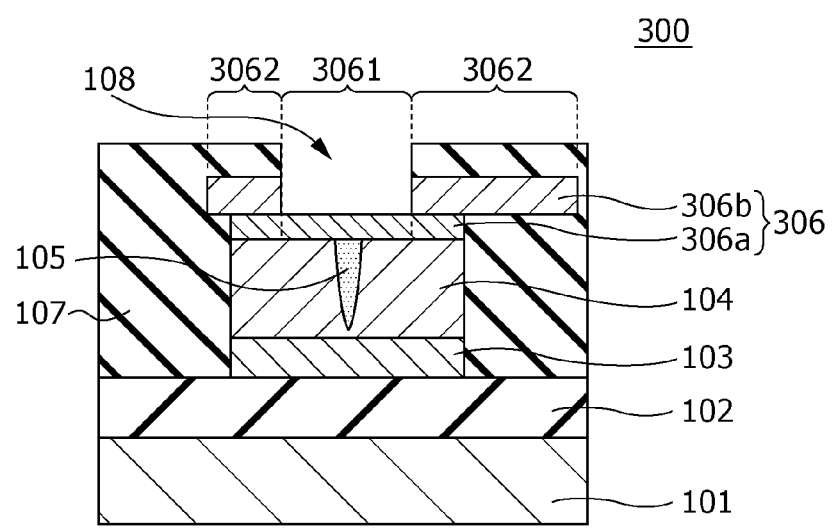
FIG. 3 is a cross-sectional view showing the structure of a gas sensor according to a modified example 2 of the first embodiment.

FIG. 3 is a cross-sectional view showing one structural example of a gas sensor 300 according to a modified example 2 of the first embodiment. Hereinafter, among constituent elements of the gas sensor 300, the same constituent element as that of the gas sensor 100 according the first embodiment or the gas sensor 200 according to the modified example 1 of the first embodiment is designated by the same reference numeral, the description thereof is omitted, and a different point will only be described.

As is the gas sensor 200, a second conductive layer 306 of the gas sensor 300 is a laminate formed of a lower layer 306a connected to the resistive film 104 and an upper layer 306b disposed on the lower layer 306a.

The lower layer 306a is provided to have an approximately flat shape with a thickness of a first portion 3061 at which the second conductive layer 306 is exposed. The upper layer 306b is provided, other than the first portion 3061, on the lower layer 306a and the insulation layer 107 in a second portion 3062 of the second conductive layer 306 which is covered with the insulation layer 107.

In the gas sensor 300, the lower layer 306a is provided to have the same size (the same shape when viewed in plan) as that of the resistive film 104, and this is a point different from the gas sensor 200.

By this structure, the lower layer 306a and the resistive film 104 can be formed by one etching step. Hence, the interface between the lower layer 306a and the resistive film 104 can be protected from intrusion of foreign substances caused by a process. As a result, the catalyst function of the lower layer 306a can be stably obtained, and a gas sensor excellent in detection of a hydrogen-containing gas can be obtained.

Modified Example 3

Figure 4A:
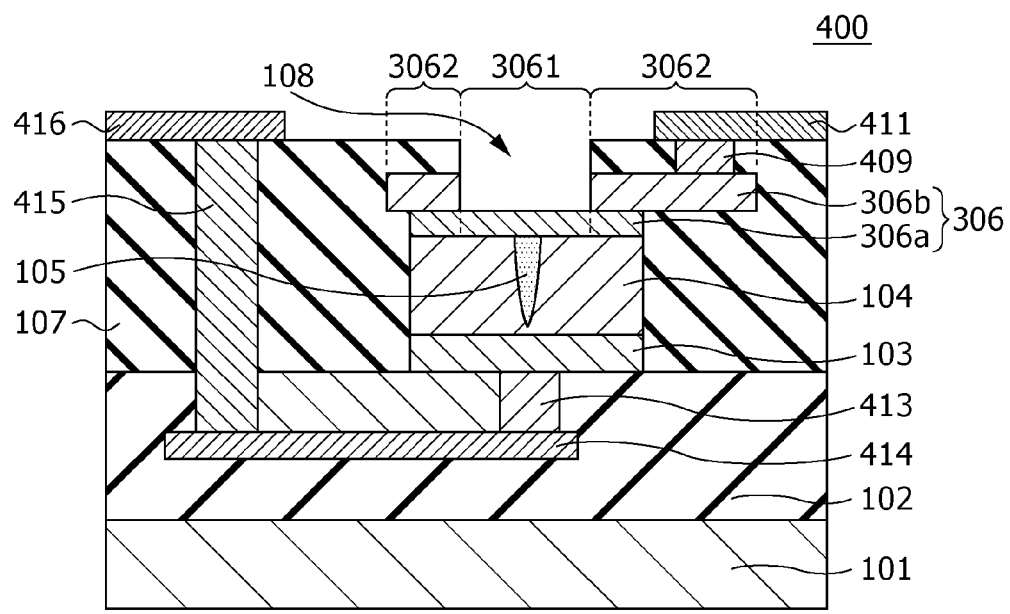
FIG. 4A is a cross-sectional view showing the structure of a gas sensor according to a modified example 3 of the first embodiment.

FIG. 4A is a cross-sectional view showing a structural example of a gas sensor 400 according to a modified example 3 of the first embodiment. Hereinafter, among constituent elements of the gas sensor 400, the same constituent element as that of the gas sensor 100 according to the first embodiment, the gas sensor 200 according to the modified example 1 of the first embodiment, or the gas sensor 300 according to the modified example 2 of the first embodiment is designated by the same reference numeral, the description thereof is omitted, and a different point will only be described.

In the gas sensor 400, various conductive members to be used for electrical connection are additionally formed in the gas sensor 300. In particular, the gas sensor 400 includes the same constituent elements as those of the gas sensor 300 at important portions and further includes a first wire 414, a second wire 416, a third wire 411, and contact plugs 409, 413, and 415.

The contact plug 413 and the first wire 414 are provided in the insulation layer 102. The contact plug 413 is connected to the first conductive layer 103 and the first wire 414. The contact plug 415 is provided in the insulation layer 102 and the insulation layer 107 and is connected to the first wire 414 and the second wire 416. The contact plug 409 is provided in the insulation layer 107 and is connected to the upper layer 306b and the third wire 411.

By the structure described above, when a detection voltage is applied between the second wire 416 and the third wire 411, a detection result of a hydrogen-containing gas can be obtained from the gas sensor 400.

In addition, besides the contact plug 409, the connection between the upper layer 306b and the third wire 411 may be obtained by a different structure. For example, as is the connection between the first conductive layer 103 and the second wire 416, the connection may be performed by two contact plugs and one wire provided in the insulation layer 102. In this case, even if the third wire 411 is not provided above the upper layer 306b, the upper layer 306b and the third wire 411 can be connected to each other.

[Supplement]

The gas sensor 100 shown in FIG. 1A includes the first conductive layer 103, the metal oxide layer 104 disposed on the first conductive layer 103, the second conductive layer 106 disposed on the metal oxide layer 104, and the insulation layer 107 which covers the layers described above.

In FIG. 1A, the second conductive layer 106 is formed of a single material. The second conductive layer 106 includes a first region 1061 (that is, the first portion 1061) and a second region 1062 (that is, the second portion 1062). The first region 1061 is a region having a relatively small thickness, and the second region 1062 is a region having a relatively large thickness. In the plan view shown in FIG. 1B, the first region 1061 is surrounded by the second region 1062. The upper surface of the second conductive layer 106 has a concave portion, and the lower surface of the second conductive layer 106 is flat. The upper surface of the first region 1061 is exposed to a gas which is to be detected.

The metal oxide layer 104 includes the local region 105 and the bulk region surrounding the local region 105. In this case, "surroundings the local region 105" is not limited to the case in which all the outer peripheral surface of the local region 105 is surrounded. In FIG. 1A, the bulk region is a region of the metal oxide layer 104 other than the local region 105. The degree of oxygen deficiency of the local region 105 is high as compared to that of the bulk region. In the plan view shown in FIG. 1B, the outline of the metal oxide layer 104 is located inside the outline of the second conductive layer 106. In FIG. 1A, the metal oxide layer 104 has a flat surface in contact with the first region 1061 and the second region 1062 of the second conductive layer 106.

The insulation layer 107 covers the first conductive layer 103, the metal oxide layer 104, and the second region 1062 of the second conductive layer 106. The insulation layer 107 does not cover the first region 1061 of the second conductive layer 106. In the example shown in FIGS. 1A and 1B, the insulation layer 107 has the opening 108 which reaches the first region 1061 of the second conductive layer 106.

The gas sensor 400 shown in FIG. 4A includes the first conductive layer 103, the metal oxide layer 104 disposed on the first conductive layer 103, the second conductive layer 306 disposed on the metal oxide layer 104, and the insulation layer 107 covering the layers described above.

In FIG. 4A, the second conductive layer 306 includes a first layer 306a (that is, the lower layer 306a) having a flat shape and a second layer 306b (that is, the upper layer 306b) disposed partially on the first layer. The boundary surface between the first layer 306a and the second layer 306b is approximately in parallel to the lower surface of the second conductive layer 306.

Figure 4B:
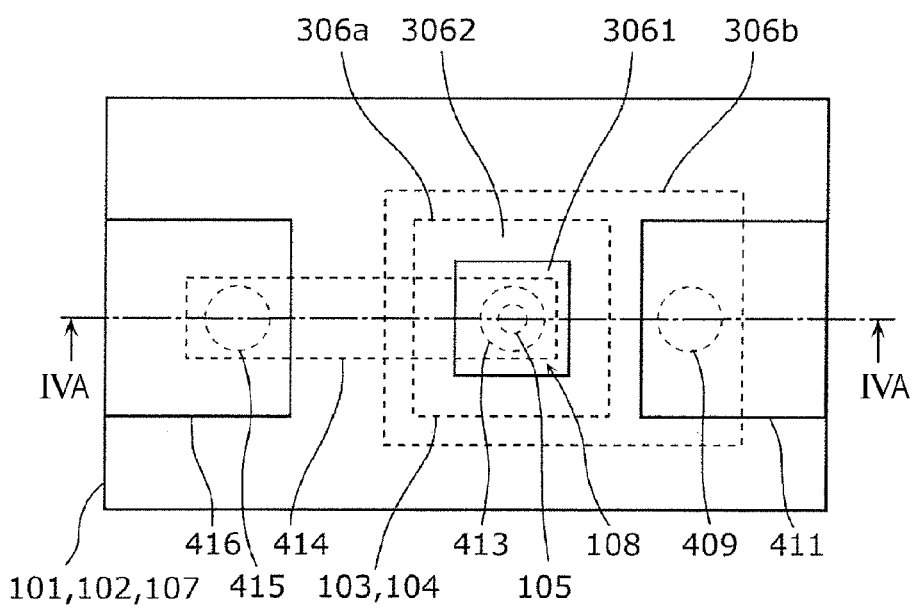
FIG. 4B is a plan view showing the structure of the gas sensor according to the modified example 3 of the first embodiment.

In addition, the second conductive layer 306 includes a first region, a second region, and a third region. The boundary surfaces between the first region, the second region, and the third region are each approximately perpendicular to the lower surface of the second conductive layer 306. In FIG. 4A, the first portion 3061 corresponds to the first region. In the second region of the second conductive layer 306, the second layer 306b is disposed on the first layer 306a. In FIG. 4A, in the second portion 3062, a region in which the first layer 306a and the second layer 306b are laminated to each other corresponds to the second region. In the third region of the second conductive layer 306, the first layer 306a is not disposed under the second layer 306b. In FIG. 4A, in the second portion 3062, a region in which the second layer 306b extends past the first layer 306a corresponds to the third region. The first region is a region having a relatively small thickness, and the second region is a region having a relatively large thickness. In the plan view shown in FIG. 4B, the first region is surrounded by the second region. In FIG. 4B, the second layer 306b has the opening which reaches the upper surface of the first layer 306a. The upper surface of the second conductive layer 306 has a concave portion, and the lower surface of the second conductive layer 306 is flat. The bottom surface of the concave portion is defined by a part of the upper surface of the first layer 306a, and the side surface of the concave portion is defined by the inner peripheral surface of the second layer 306b. In the plan view shown in FIG. 4B, the outline of the first layer 306a is located inside the outline of the second layer 306b.

In the example shown in FIG. 4A, the gas sensor 400 includes the plug 409 penetrating the insulation layer 107 and the wire 411 provided on the insulation layer 107 and the plug 409. The plug 409 electrically connects the third region of the second conductive layer 306 to the wire 411.

[Manufacturing Method and Operation of Gas Sensor]

Next, with reference to FIGS. 5A to 5I, one example of a manufacturing method of the gas sensor 400 will be described. In addition, the following manufacturing method is not only applied to the manufacturing of the gas sensor 400 but may also be applied to the manufacturing of the gas sensor 100, 200, or 300 after being partially appropriately modified.

Figure 5A:
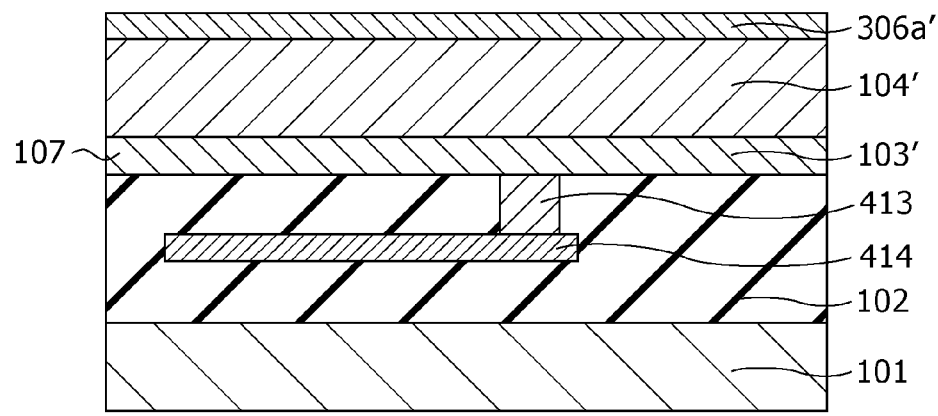
FIG. 5A is a cross-sectional view showing a method for manufacturing the gas sensor according to the modified example 3 of the first embodiment.

First, as shown in FIG. 5A, in a step of forming the first wire 414, on the substrate 101 on which a transistor, an underlayer wire, and the like are formed, the insulation layer 102 is formed. In the first insulation layer 102, an conductive layer formed of aluminum or the like having a thickness of 400 to 600 nm is formed and is then patterned, so that the first wire 414 is formed. In addition, in a step of forming the contact plug 413, patterning is performed using a desired mask, so that the contact plug 413 connected to the first wire 414 is formed in the insulation layer 102.

In addition, on the insulation layer 102, an conductive layer 103' to be formed into the first conductive layer 103 is formed. As the conductive layer 103', for example, a TaN thin film having a thickness of 100 nm may be formed by a sputtering method. In addition, between the conductive layer 103' and the insulation layer 102, an adhesive layer may be formed from Ti, TiN, or the like by a sputtering method.

Subsequently, on the conductive layer 103', a metal oxide layer 104' to be formed into the resistive film 104 is formed. As the metal oxide layer 104', for example, an oxygen deficient-type tantalum oxide layer may be formed by a reactive sputtering method using a Ta target or the like. The tantalum oxide layer has a high initial resistance when the thickness thereof is excessively large, and when the thickness is excessively small, a stable resistance change may not be obtained; hence the thickness may be set in a range of 1 to 8 nm.

Next, on the metal oxide layer 104', an conductive layer 306a' to be formed into the lower layer 306a is formed. As the conductive layer 306a', for example, a Pt thin film having a thickness of 15 nm may be formed by a sputtering method.

Figure 5B:
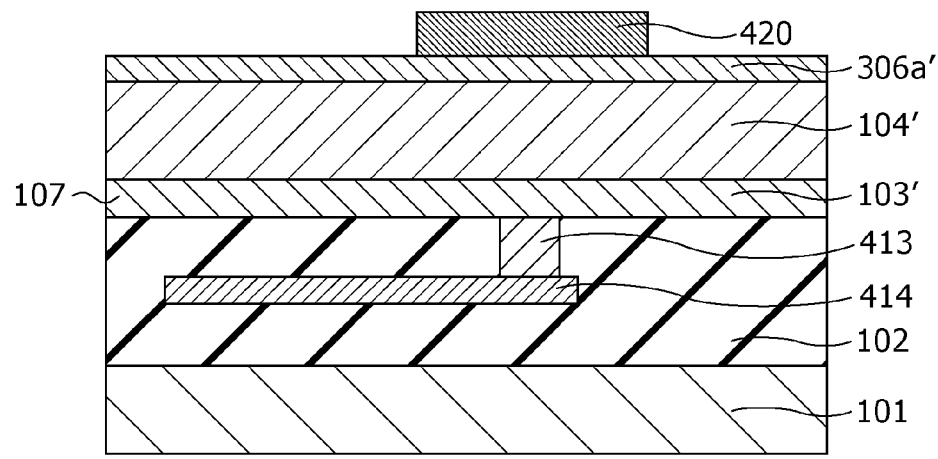
FIG. 5B is a cross-sectional view showing the method for manufacturing the gas sensor according to the modified example 3 of the first embodiment.

Next, as shown in FIG. 5B, by a photolithographic step, a mask 420 is formed above the contact plug 413 using a photoresist.

Figure 5C:
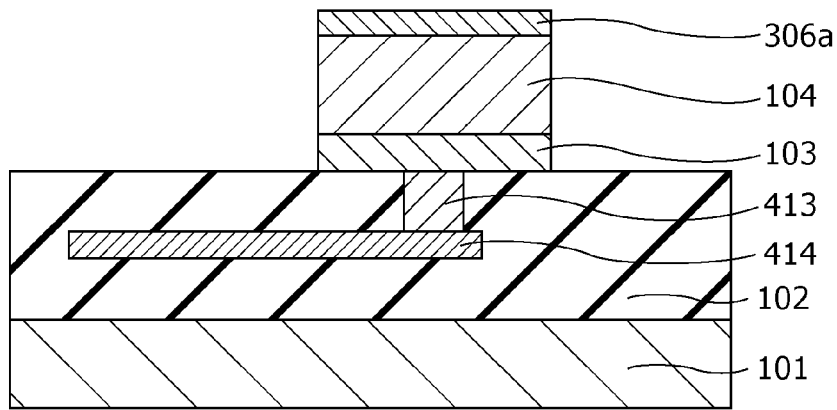
FIG. 5C is a cross-sectional view showing the method for manufacturing the gas sensor according to the modified example 3 of the first embodiment.

Next, as shown in FIG. 5C, by dry etching using the mask 420, the conductive layer 103', the metal oxide layer 104', and the conductive layer 306a' are formed to have an element shape, so that the first conductive layer 103, the resistive film 104, and the lower layer 306a are formed.

Figure 5D:
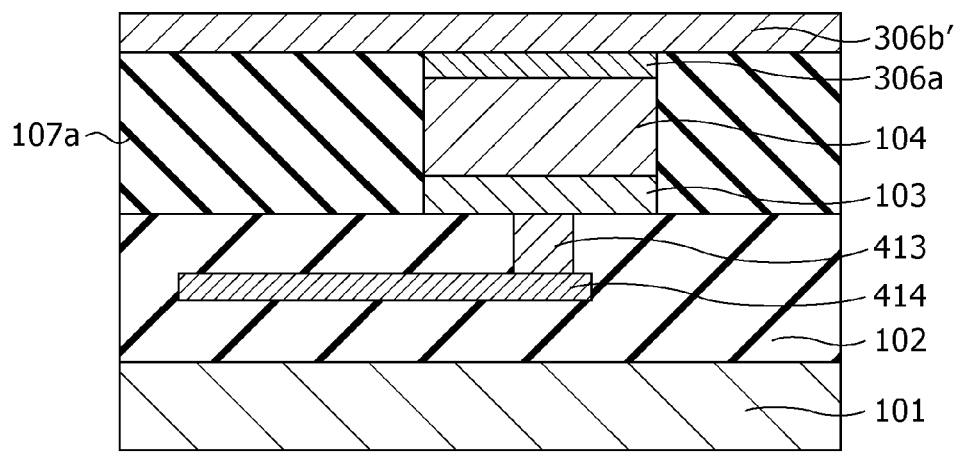
FIG. 5D is a cross-sectional view showing the method for manufacturing the gas sensor according to the modified example 3 of the first embodiment.

Subsequently, as shown in FIG. 5D, an insulation layer 107a is deposited on the insulation layer 102. Next, by chemical mechanical polishing (CMP), the insulation layer 107a is etched back so as to expose the lower layer 306a. On the insulation layer 107a, an conductive layer 306b' to be formed into the upper layer 306b is formed so as to be in contact with the lower layer 306a. As the conductive layer 306b', for example, a TiN thin film having a thickness of 150 nm may be formed by a sputtering method.

Figure 5E:
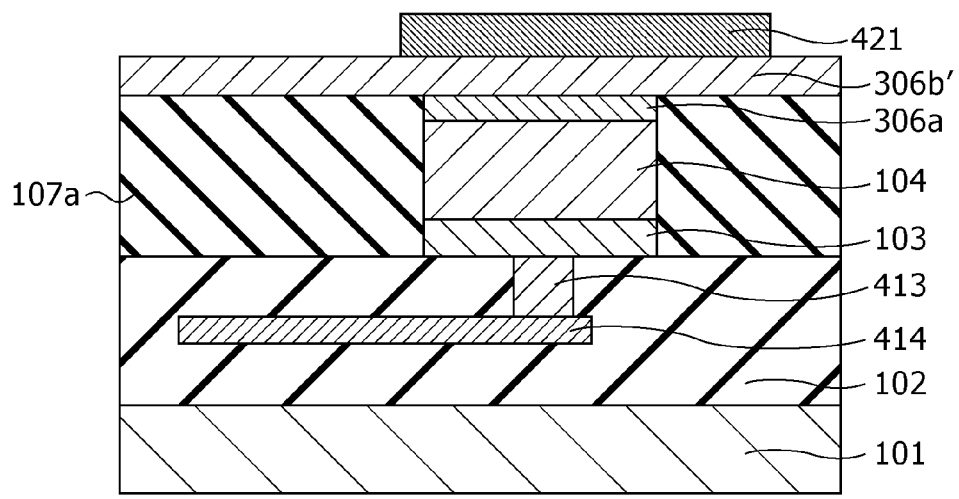
FIG. 5E is a cross-sectional view showing the method for manufacturing the gas sensor according to the modified example 3 of the first embodiment.

Next, as shown in FIG. 5E, by a photolithographic step, a mask 421 is formed on the conductive layer 306b' using a photoresist in a region including a position located above the lower layer 306a.

Figure 5F:
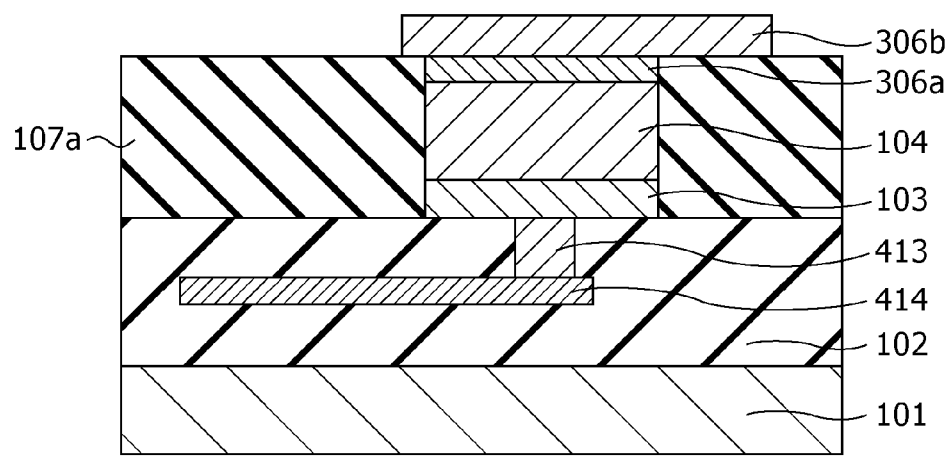
FIG. 5F is a cross-sectional view showing the method for manufacturing the gas sensor according to the modified example 3 of the first embodiment.

Subsequently, as shown in FIG. 5F, by dry etching using the mask 421, the conductive layer 306b' is formed into the upper layer 306b.

Figure 5G:
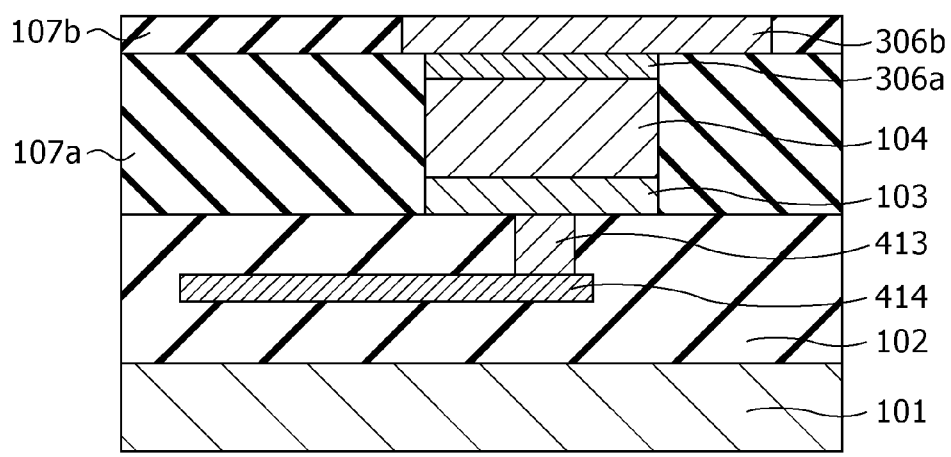
FIG. 5G is a cross-sectional view showing the method for manufacturing the gas sensor according to the modified example 3 of the first embodiment.

Next, as shown in FIG. 5G, on the insulation layer 107a and the upper layer 306b, an insulation layer 107b is deposited. Subsequently, by using CMP, the insulation layer 107b is etched back until the upper layer 306b is exposed.

Figure 5H:
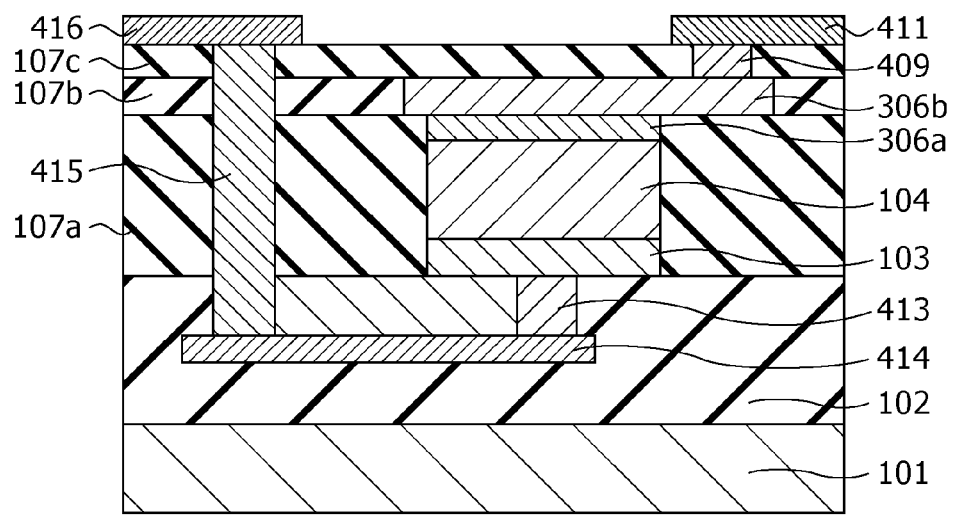
FIG. 5H is a cross-sectional view showing the method for manufacturing the gas sensor according to the modified example 3 of the first embodiment.

Next, as shown in FIG. 5H, on the insulation layer 107b and the upper layer 306b, an insulation layer 107c is deposited. A via (through-hole) which reaches the upper surface of the upper layer 306b is formed in the insulation layer 107c, and an conductive material is filled in the via to form the contact plug 409. In addition, a via which reaches the upper surface of the first wire 414 is formed through the insulation layers 107a to 107c, and an conductive material is filled in this via to form the contact plug 415. Furthermore, a new conductive film is disposed on the insulation layer 107c and is then patterned, so that the third wire 411 connected to the contact plug 409 and the second wire 416 connected to the contact plug 415 are formed.

Figure 5I:
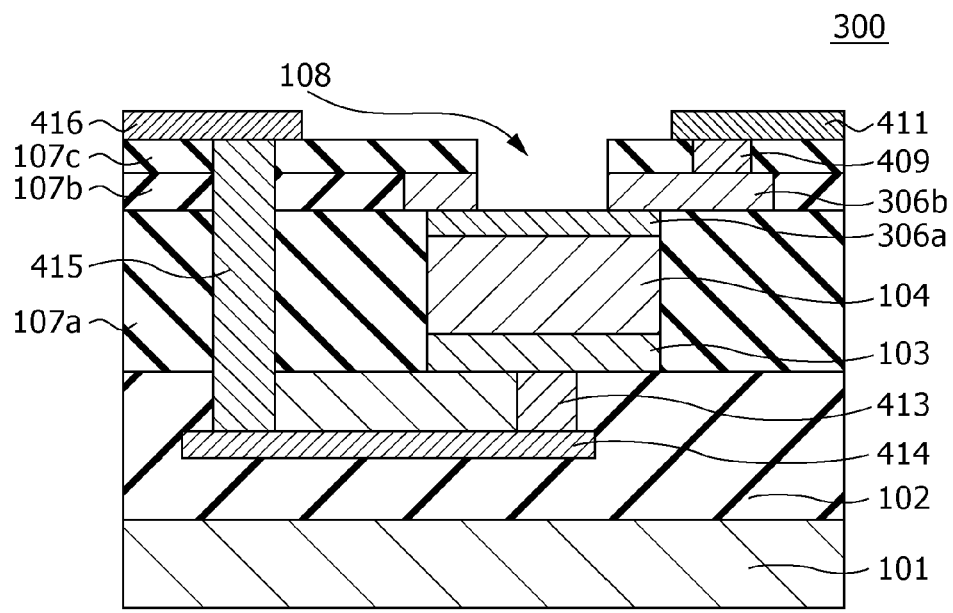
FIG. 5I is a cross-sectional view showing the method for manufacturing the gas sensor according to the modified example 3 of the first embodiment.

Subsequently, as shown in FIG. 5I, by performing etching, parts of the insulation layer 107c and the upper layer 306b located above the lower layer 306a are removed, so that the opening 108 through which the upper surface of the lower layer 306a is partially exposed is formed.

Next, by applying an initial break voltage between the second wire 416 and the third wire 411, the local region 105 is formed in the resistive film 104, so that the gas sensor 400 shown in FIG. 4A is formed.

Hereinafter, as for one example of the resistance change characteristic of the gas sensor 100 by voltage application, actual measurement results obtained by a sample element will be described. In addition, the resistance change characteristic of the gas sensor 100 by a hydrogen-containing gas will be described later.

Figure 6:
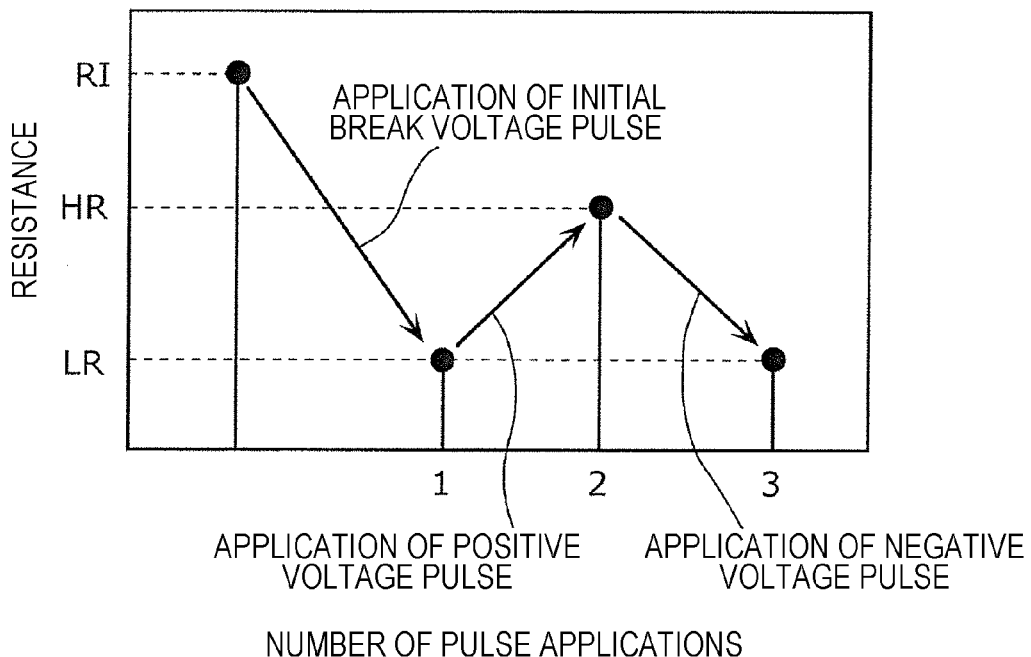
FIG. 6 is a graph showing the state of the gas sensor according to the modified example 3 of the first embodiment.

FIG. 6 is a graph showing a resistance change characteristic actually measured using a sample element.

In the gas sensor 400 which is a sample element, the measurement results of which are obtained as shown in FIG. 6, the size of each of the first conductive layer 103, the lower layer 306a, and the resistive film 104 is set to 0.5 μm by 0.5 μm (area: 0.25 μm$^2$). In addition, when the composition of a tantalum oxide used as the resistive film 104 is represented by TaO$_y$, y is set to 2.47. Furthermore, the thickness of the resistive film 104 is set to 5 nm. By using the gas sensor 400 as described above, when a reading voltage (such as 0.4 V) is applied between the first conductive layer 103 and the lower layer 306a, an initial resistance RI is approximately $10^7$ to $10^8 \Omega$.

As shown in FIG. 6, when the resistance of the gas sensor 400 is the initial resistance RI (higher than a resistance HR in a high resistive state), by applying the initial break voltage between the first conductive layer 103 and the lower layer 306a, the resistive state is changed. Subsequently, as a writing voltage, for example, when two types of voltage pulses (a positive voltage pulse and a negative voltage pulse) having a pulse width of 100 ns and different polarities are alternately applied between the first conductive layer 103 and the lower layer 306a of the gas sensor 400, the resistance of the resistive film 104 is reversibly changed.

That is, as a writing voltage, when a positive voltage pulse (pulse width: 100 ns) is applied between the conductive layers, the resistance of the resistive film 104 is increased from a low resistance LR to the high resistance HR. On the other hand, as a writing voltage, when a negative voltage pulse (pulse width: 100 ns) is applied between the conductive layers, the resistance of the resistive film 104 is decreased from the high resistance HR to the low resistance LR. In addition, as for the polarity of the voltage pulse, when the potential of the upper layer 306b is high as compared to that of the first conductive layer 103, the polarity is "positive", and when the potential of the lower layer 306a is low as compared to that of the first conductive layer 103, the polarity is "negative".

By the use of the resistance change characteristic obtained by the voltage application as described above, before monitoring of a hydrogen-containing gas is started, when a positive voltage pulse is applied between the first conductive layer 103 and the lower layer 306a, a hydrogen-containing gas can be detected using the gas sensor 400 which is set in the high resistive state (HR). Accordingly, compared to the case in which a hydrogen-containing gas is detected using the gas sensor 400 which is set in the low resistive state (LR), the decrease in resistance can be more clearly detected; hence, detection performance of a hydrogen-containing gas is improved.

Modified Example 4

Figure 7:
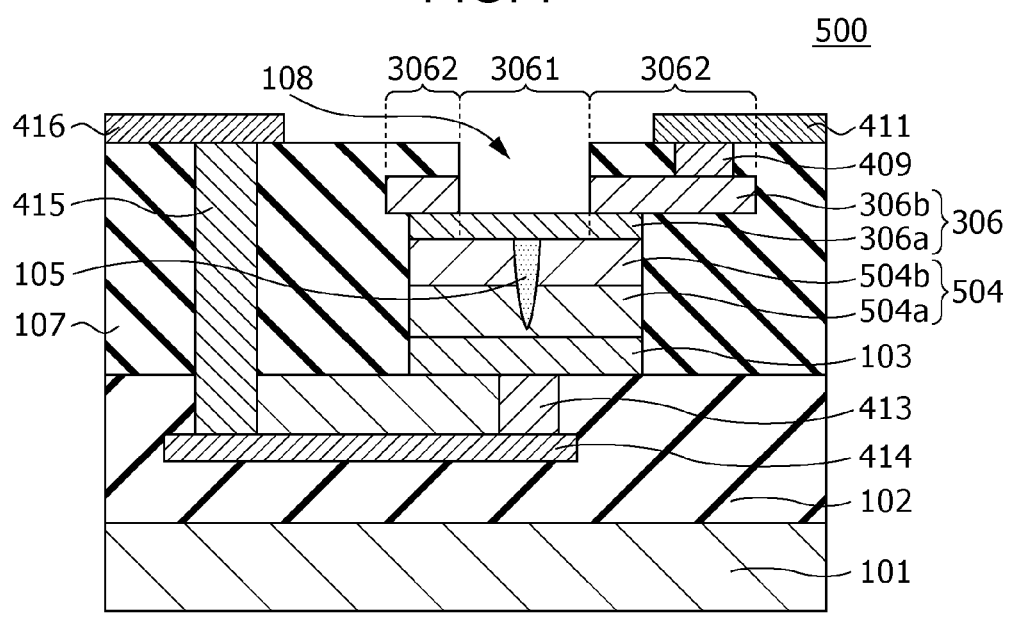
FIG. 7 is a cross-sectional view showing a gas sensor according to a modified example 4 of the first embodiment.

FIG. 7 is a cross-sectional view showing one structural example of a gas sensor 500 according to a modified example 4 of the first embodiment. Hereinafter, among constituent elements of the gas sensor 500, the same constituent element as that of the gas sensor 100 according the first embodiment, the gas sensor 200 according to the modified example 1 of the first embodiment, the gas sensor 300 according to the modified example 2 of the first embodiment, or the gas sensor 400 according to the modified example 3 of the first embodiment is designated by the same reference numeral, the description thereof is omitted, and a different point will only be described.

The gas sensor 500 of this modified example 4 is different from the gas sensor 400 since a resistive film 504 is a laminate formed of a first oxide layer 504a in contact with the first conductive layer 103 and a second oxide layer 504b in contact with the lower layer 306a. In addition, the resistive film 504 may be a laminate containing not only two layers but also at least three layers.

In the first oxide layer 504a and the second oxide layer 504b, the local region 105 is provided in which in response to the application of an electrical pulse and a hydrogen-containing gas, the degree of oxygen deficiency is reversibly changed. The local region 105 is formed to penetrate at least the second oxide layer 504b and to be in contact with the lower layer 306a.

In other words, the resistive film 504 has a laminate structure at least containing a first metal oxide layer 504a containing a first metal oxide and a second metal oxide layer 504b containing a second metal oxide. In addition, the first metal oxide layer 504a is disposed between the first conductive layer 103 and the second metal oxide layer 504b, and the second metal oxide layer 504b is disposed between the first metal oxide layer 504a and the lower layer 306a.

The thickness of the second metal oxide layer 504b may be smaller than that of the first metal oxide layer 504a. In this case, the local region 105 can be easily formed so as not to be in contact with the first conductive layer 103. The degree of oxygen deficiency of the second metal oxide layer 504b may be low as compared to that of the first metal oxide layer 504a. In this case, since the resistance of the second metal oxide layer 504b is higher than that of the first metal oxide layer 504a, the voltage applied to the resistive film 504 is mostly applied to the second metal oxide layer 504b. By the structure described above, for example, the initial break voltage can be concentrated to the second metal oxide layer 504b, and hence, the initial break voltage required to form the local region 105 can be effectively decreased.

In addition, in the present disclosure, when the metal forming the first metal oxide layer 504a is the same as that forming the second metal oxide layer 504b, instead of using the "degree of oxygen deficiency", the term "oxygen content" may be used in some cases. The "high oxygen content" corresponds to the "low degree of oxygen deficiency", and the "low oxygen content" corresponds to the "high degree of oxygen deficiency".

However, as described below, the resistive film 504 according to this embodiment is not limited to the case in which the metal forming the first metal oxide layer 504a is the same as that forming the second metal oxide layer 504b, and the metal of the metal oxide layer 504a may be different from the metal of the second metal oxide layer 504b. That is, the first metal oxide layer 504a and the second metal oxide layer 504b may be formed from oxides containing different metals from each other.

When a first metal forming the first metal oxide layer 504a is the same as a second metal forming the second metal oxide layer 504b, the oxygen content inversely corresponds to the degree of oxygen deficiency. That is, when the oxygen content of the second metal oxide is higher than that of the first metal oxide, the degree of oxygen deficiency of the second metal oxide is lower than that of the first metal oxide.

The resistive film 504 includes the local region 105 in the vicinity of the interface between the first metal oxide layer 504a and the second metal oxide layer 504b. The degree of oxygen deficiency of the local region 105 is high as compared to that of the second metal oxide layer 504b and is different from the degree of oxygen deficiency of the first metal oxide layer 504a.

By application of the initial break voltage between the first conductive layer 103 and the lower layer 306a, the local region 105 is formed in the resistive film 504 having a laminate structure of the first metal oxide layer 504a and the second metal oxide layer 504b. By the initial break voltage, there can be formed the local region 105 which is in contact with the lower layer 306a, which penetrates the second metal oxide layer 504b and partially enters the first metal oxide layer 504a, and which is not in contact with the first conductive layer 103.

Modified Example 5

Figure 8A:
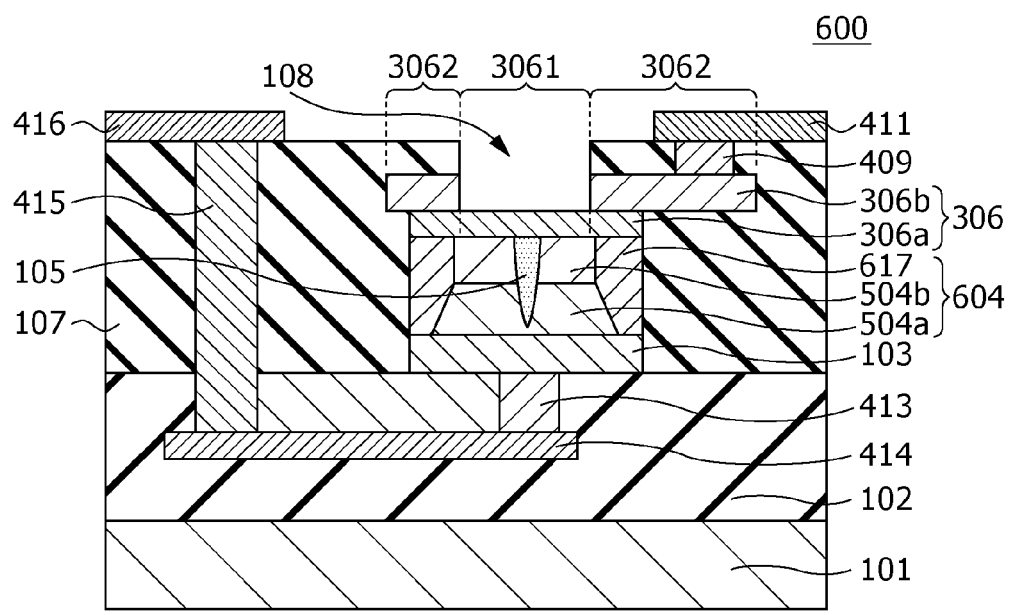
FIG. 8A is a cross-sectional view showing a gas sensor according to a modified example 5 of the first embodiment.
Figure 8B:
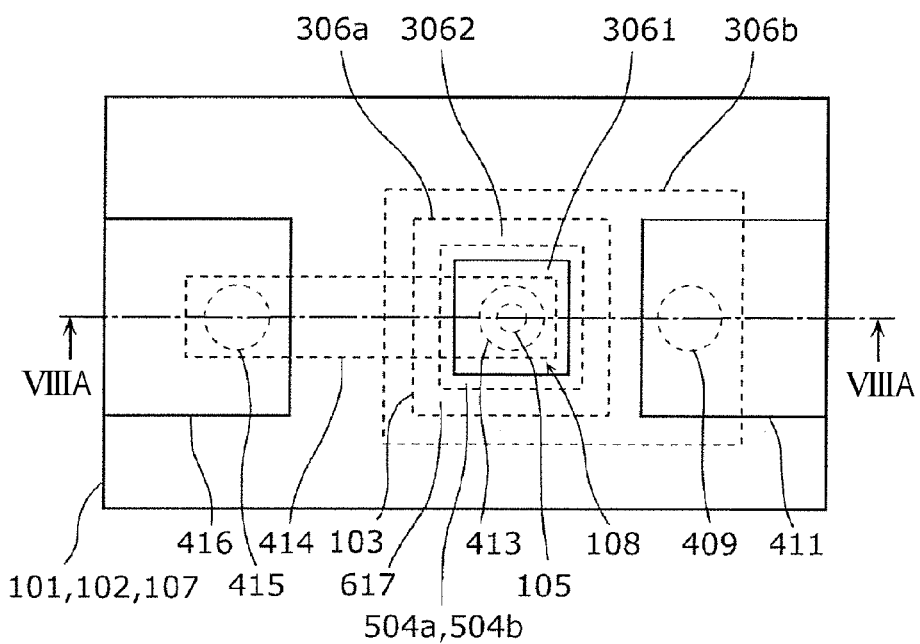
FIG. 8B is a plan view showing the gas sensor according to the modified example 5 of the first embodiment.

FIG. 8A is a cross-sectional view showing one structural example of a gas sensor 600 according to a modified example 5 of the first embodiment. FIG. 8B is a plan view showing one structural example of the gas sensor 600 according to the modified example 5 of the first embodiment. The cross-section of FIG. 8A corresponds to a cross-section viewed in an arrow direction along the section line VIIIA-VIIIA of FIG. 8B. Hereinafter, among constituent elements of the gas sensor 600, the same constituent element as that of the gas sensor 100 according the first embodiment, the gas sensor 200 according to the modified example 1 of the first embodiment, the gas sensor 300 according to the modified example 2 of the first embodiment, the gas sensor 400 according to the modified example 3 of the first embodiment, or the gas sensor 500 according to the modified example 4 of the first embodiment is designated by the same reference numeral, the description thereof is omitted, and a different point will only be described.

Since having an oxide film 617 along the periphery of the resistive film 504, the gas sensor 600 according to this modified example 5 is different from the gas sensor 500. The oxide film 617 is formed, for example, by oxidizing the first metal oxide layer 504a and the second metal oxide layer 504b from the side surfaces thereof and has a higher resistance than that of the first metal oxide layer 504a. In addition, instead of using the oxide film 617, an oxynitride film may also be formed by nitriding the first metal oxide layer 504a and the second metal oxide layer 504b from the side surfaces thereof.

Since the oxide film 617 having a high resistance is formed on the side surface portion of the resistive film 504, a contact area at which the first metal oxide layer 504a and the second metal oxide layer 504b, each of which has a low resistance, are in contact with each other becomes smaller than the area of the lower layer 306a. The contact area described above may be either smaller or larger than that of the opening 108.

By the structure described above, the current density of a current flowing from the first metal oxide layer 504a to the second metal oxide layer 504b is increased. As a result, the initial break voltage of the gas sensor is decreased, and the initial break at a low voltage can be realized. Furthermore, since the local region 105 is formed in the region of the opening 108, the time required for hydrogen contained in a gas to be inspected to reach the local region 105 can be shortened.

As for the gas sensor 600 formed as described above, one evaluation example of the resistance change characteristic by a hydrogen-containing gas will be described.

Figure 9A:
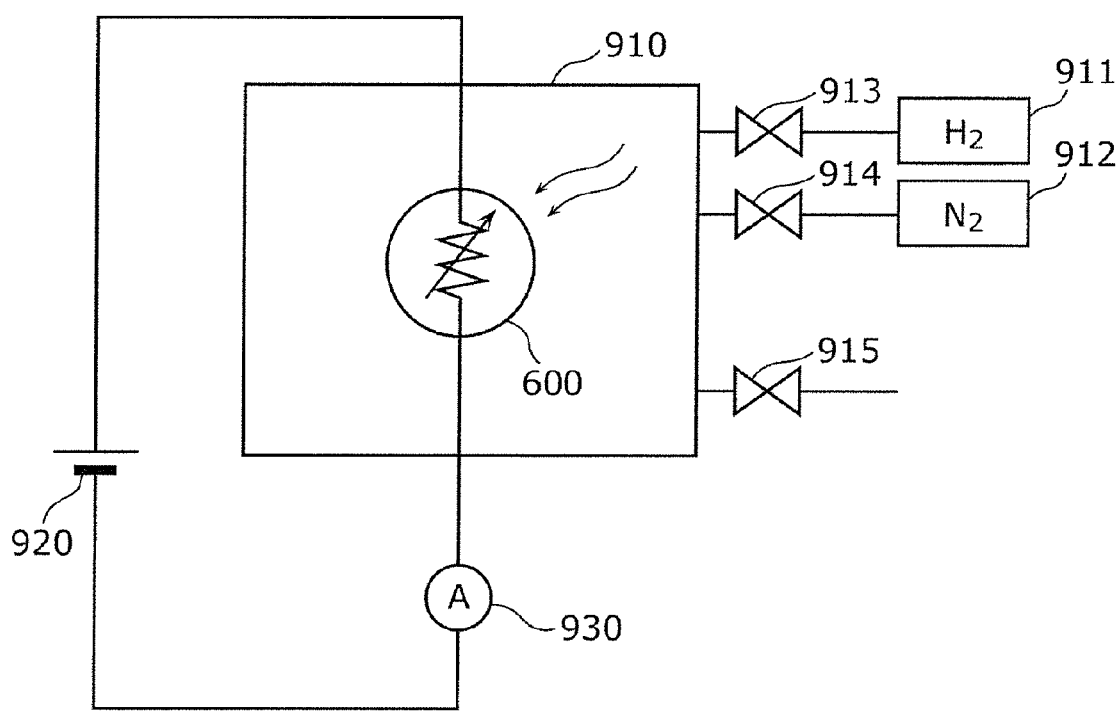
FIG. 9A is a circuit diagram showing an evaluation system of the gas sensor according to the modified example 5 of the first embodiment.

FIG. 9A is a block diagram showing one example of an evaluation system used for the evaluation of the gas sensor 600. An evaluation system 900 shown in FIG. 9A includes an air-tight container 910 receiving the gas sensor 600, a power source 920, and a current meter 930. The air-tight container 910 is connected to a hydrogen cylinder 911 and a nitrogen cylinder 912 through introduction valves 913 and 914, respectively, and is also configured so that a gas in the container 910 is dischargeable through an exhaust valve 915.

Figure 9B:
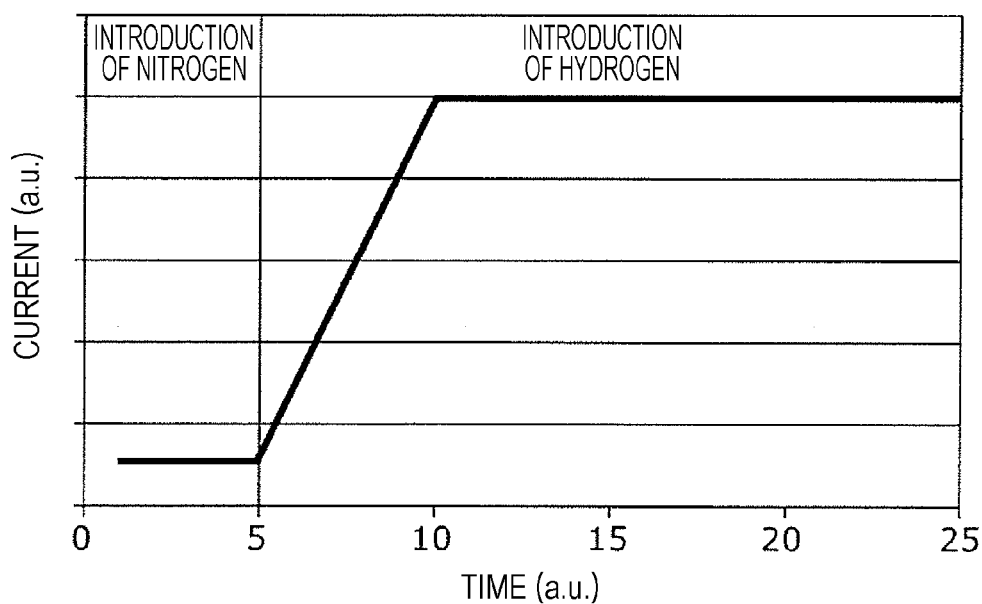
FIG. 9B is a graph showing an evaluation result of the gas sensor according to the modified example 5 of the first embodiment.

FIG. 9B is a graph showing one evaluation result of the gas sensor 600. The horizontal axis indicates the time (a.u.), and the vertical axis indicates a current (a.u.) flowing between the first conductive layer 103 and the lower layer 306a. In this experiment, first, a nitrogen gas was charged into the air-tight container 910 in which the gas sensor 600 was placed, and a hydrogen gas was then charged.

FIG. 9B shows the result of this evaluation, and along the horizontal axis, two types of periods, that is, the period for nitrogen introduction and the period of hydrogen introduction, are shown. It is found that after the introduction gas was switched from a nitrogen gas to a hydrogen gas, the current was started to increase.

In this evaluation example, a predetermined voltage (potential difference) was applied between the first conductive layer 103 and the lower layer 306a, and as a result, the local region 105 was set in advance in a high resistive state. In operation of monitoring a hydrogen-containing gas, a detection voltage of 0.6 V was applied between the first conductive layer 103 and the lower layer 306a. In the state in which a hydrogen gas is detected, a current of 10 to 200 μA flowed between the first conductive layer 103 and the lower layer 306a. Hence, it is found that by the gas sensor 600, a hydrogen-containing gas can be monitored by a significantly small power consumption of at most 0.006 to 0.12 mW.

In addition, when a detection voltage of 0.4 V was applied between the first conductive layer 103 and the lower layer 306a, the resistance was not changed by a hydrogen gas, and a hydrogen gas could not be detected. The reason for this is believed that the amount of heat generated in the local region 105 is not sufficient by the application of a detection voltage of 0.4 V, and the catalyst function of the lower layer 306a is not sufficiently facilitated. It is believed that for detection of a hydrogen gas, for example, a detection voltage of 0.6 V or more is required to be applied.

From the results described above, the detection mechanism of a hydrogen gas by the gas sensor 600 can be considered as follows.

When a hydrogen-containing gas is brought into contact with the second conductive layer 306 (in particular, the lower layer 306a), by the catalyst function of the lower layer 306a, a hydrogen atom is dissociated from a hydrogen-containing gas. In order to maintain the equilibrium, the hydrogen atom thus dissociated diffuses in the lower layer 306a and reaches the local region 105.

By this hydrogen atom, a reduction reaction occurs in the minute local region 105, and the degree of oxygen deficiency in the local region 105 is increased. As a result, filaments in the local region 105 are likely to be linked with each other, so that the resistance of the local region 105 is decreased. As a result, it is believed that a current flowing between the first conductive layer 103 and the lower layer 306a is increased.

In addition, it is also believed that the operation described above is performed not only in the gas sensor 600 but also in the gas sensors 100, 200, 300, 400 and 500, the important portion of each of which has substantially the same structure as that of the gas sensor 600. In addition, it is also believed that a detectable gas is not limited to a hydrogen gas, and that the operation described above may also be performed for various types of hydrogen-containing gases, such as methane and an alcohol.

As described above, according to the gas sensor 600 of this embodiment, a sensor excellent in electrical power saving can be obtained in which heat generation is performed only by a current used for detecting the resistive state, and without performing heating by an additional heater, a hydrogen-containing gas can be detected.

[Dependence of Detection Time of Hydrogen-Containing Gas on Thickness of Second Conductive Layer]

The dependence of a time required for detection of a hydrogen-containing gas of a gas sensor on the thickness of the second conductive layer will be described based on the mechanism in which the gas sensor detects a hydrogen-containing gas. In addition, in order to facilitate the understanding, by the use of a gas sensor 700 shown in FIG. 10A in which a resistive film 704 is formed of a single layer, the mechanism will be described; however, the following description may also be applied to a gas sensor in which the resistive film 704 is formed from a plurality of layers.

Figure 10A:
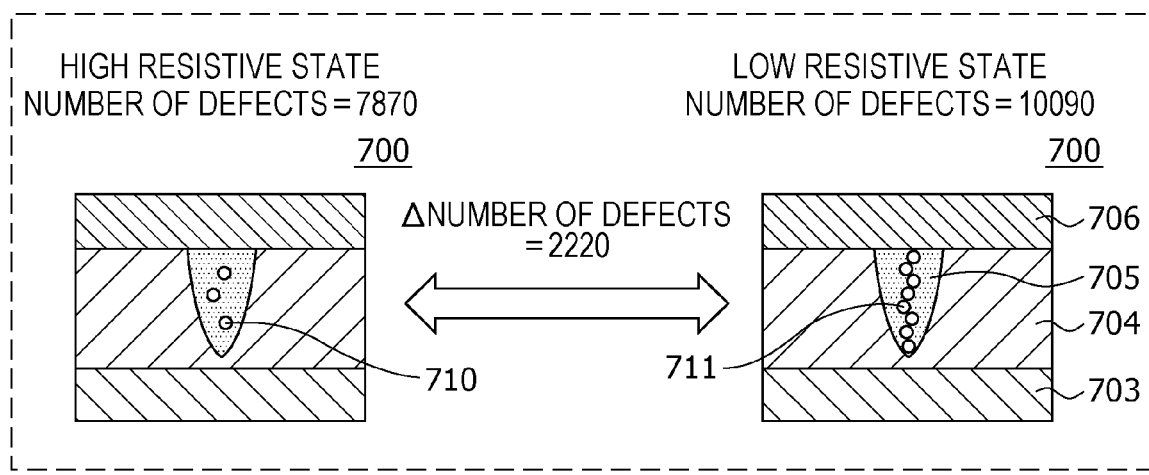
FIG. 10A is a schematic view showing a resistive state and an oxygen defect state of a gas sensor.

FIG. 10A is a schematic view showing the resistive state and the oxygen defect state of the gas sensor 700. FIG. 10A shows the fundamental gas sensor 700 formed of a first conductive layer 703, the resistive film 704, a local region 705, and a second conductive layer 706.

As schematically shown in FIG. 10A, it is estimated from the evaluation result obtained by the simulation performed by the present inventor that in the local region 705 of the gas sensor 700 which is maintained in a high resistive state having an average resistance of approximately 40 kΩ, approximately 7,870 oxygen defects 710 are present. In the state described above, the number of the oxygen defects 710 in the local region 705 is not sufficient to form the filament, and the gas sensor 700 is maintained in a high resistive state.

When the number of the oxygen defects 710 present in the local region 705 in a low resistive state is evaluated by the simulation, the low resistive state being obtained from the above high resistive state in such a way that a hydrogen gas (hydrogen atoms) is allowed to reach the local region 705 after passing through the second conductive layer 706 so that the resistance is decreased by approximately one digit, it is estimated that the number of the oxygen defects 710 is increased to approximately 10,090. When a hydrogen atom reaches the local region 705, this hydrogen atom reacts with oxygen in the local region 705, and as a result, a new oxygen defect 711 is generated. When the oxygen defect 711 and the existing oxygen defect 710 are linked with each other, a filament is formed, and the gas sensor 700 is changed into a low resistive state.

Accordingly, in order to decrease the resistance of the gas sensor 700 by approximately one digit, the number (such as 10,090−7,870=2,220) of hydrogen molecules approximately equivalent to the number of increased oxygen defects is required to reach the local region 705.

Figure 10B:
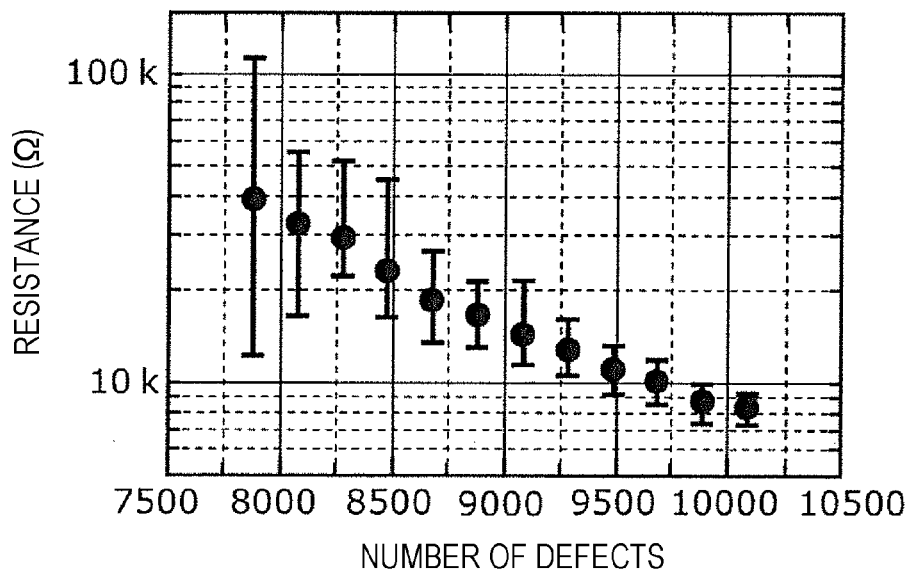
FIG. 10B is a graph showing the relationship between the resistance of the gas sensor and the number of oxygen defects.

FIG. 10B is a graph showing the relationship between the resistance of the gas sensor 700 and the number of oxygen defects present in the local region 705.

The number of hydrogen molecules which reach the local region 705 can be calculated by the following Equation 1 in consideration of the diffusion of hydrogen molecules in the second conductive layer 706. In addition, in Equation 1, the case in which the second conductive layer 706 is formed from platinum (Pt) is assumed.

$$n = N_0 p A \sqrt{\frac{N_A K_B T}{2 \Pi M}} \, \mathrm{erfc}\left(\frac{x}{2\sqrt{D_{Pt} t}}\right)$$ Equation 1

$x$: thickness of second conductive layer, $t$: time, $p$: hydrogen concentration, $A$: area of local region Constants at 1 atm and 25° C. when second conductive layer is formed of Pt

| Parameter (1 atm 25° C.) | | Value | Unit |
| --- | --- | --- | --- |
| Number of gas molecules per unit volume | $N_0$ | $2.46 \times 10^{19}$ | $cm^{-3}$ |
| Molecular weight of hydrogen | $M$ | 2.02 | $gmol^{-1}$ |
| Diffusion coefficient of hydrogen in Pt [1], [2] | $D_{Pt}$ | $1.45 \times 10^{12} \sqrt{P_{H2}}$ | $cm^{-2}s^{-1}$ |
| Avogadro constant | $N_A$ | $6.02 \times 10^{23}$ | |
| Boltzmann constant | $K_B$ | $1.38 \times 10^{-23}$ | $JK^{-1}$ |

[1] S. Uemiya, Topics in Catalysis 29, 79, 2004
[2] J. D. Fast Interaction of Metals and Gasses 1965

In accordance with Equation 1, the number of hydrogen molecules per unit time which reaches the local region 705 by diffusion through the second conductive layer 706 is influenced by a number $N_0$ of hydrogen molecules contained in a gas to be inspected in contact with the second conductive layer 706 and a thickness x of the second conductive layer 706.

Figure 11:
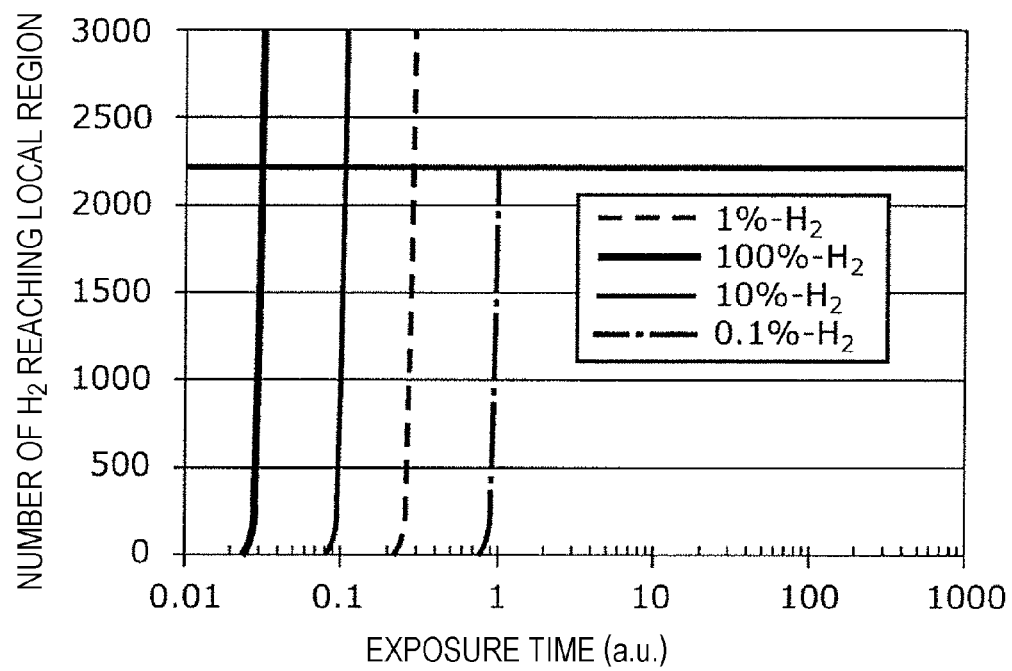
FIG. 11 is a graph showing the relationship between an exposure time of the gas sensor to a hydrogen-containing gas and the number of hydrogen molecules which reach a local region.

FIG. 11 is a graph showing the relationship between an exposure time of the gas sensor 700 to a hydrogen-containing gas and the number of hydrogen molecules which reach the local region 705. In the case in which, for example, the thickness of the second conductive layer 706 formed from platinum is set to 18.6 nm, the exposure time dependence of the number (hereinafter, referred to as $N(H_2)$) of hydrogen molecules which reach the local region 705 is shown. In FIG. 11, the exposure time dependences at four concentrations, that is, 0.1%, 1%, 10%, and 100%, are shown. From FIG. 11, it is found that when a critical time corresponding to each hydrogen concentration passes, $N(H_2)$ is rapidly increased. In addition, as the concentration of hydrogen in a gas to be measured is increased, the rise time of $N(H_2)$ is shortened.

FIG. 11 shows that when the concentration of hydrogen in a gas to be inspected is high, that is, when the number $N_0$ of hydrogen molecules is large, the number of hydrogen molecules required to form filaments rapidly reaches the local region 705, and hence the gas sensor 700 is changed into a low resistive state in a short time.

Figure 12:
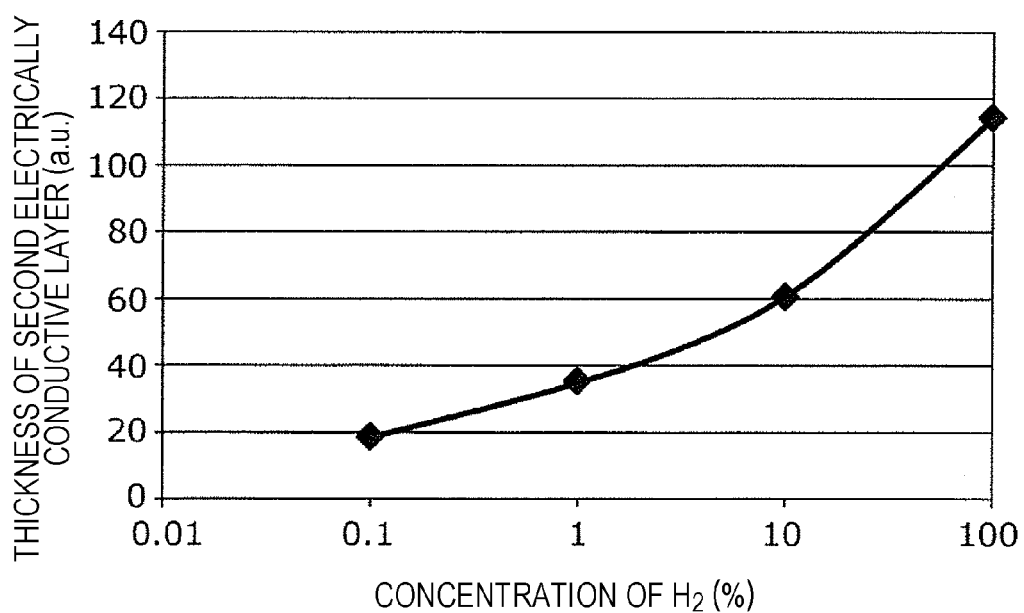
FIG. 12 is a graph showing the relationship between a hydrogen gas concentration and the thickness of a second conductive layer at which the resistance of the gas sensor is changed after one second from the start of gas introduction.

As one example, FIG. 12 shows a calculation result showing the relationship between the thickness of the second conductive layer 706 and the concentration of a hydrogen gas at which the number (such as 2,220) of hydrogen molecules required to form filaments reaches the local region 705 after one second from the introduction of a hydrogen gas (that is, exposure to a hydrogen gas is performed for one second).

FIG. 12 shows that even if the concentration of hydrogen in a gas to be inspected is low, when the thickness of the second conductive layer 706 is small, the number (such as 2,220) of hydrogen molecules required to form filaments reaches the local region within one second.

Hence, when the second conductive layer 706 is formed to have a thickness at which the number of hydrogen molecules required for the resistance change of the resistive film 704 passes therethrough for a predetermined time, a hydrogen gas at a desired concentration can be detected within a predetermined time.

As described above, by the use of the gas sensors 100 to 600 described in the embodiment and the modified examples, when the second conductive layer 106 or the lower layer 206a or 306a is formed to have a small thickness, a gas sensor excellent in detection of a hydrogen-containing gas can be obtained in which the detection time of a hydrogen-containing gas can be shortened, and a hydrogen-containing gas at a lower concentration can be detected.

Second Embodiment

A fuel-cell vehicle according to a second embodiment comprises one of the gas sensors described in the first embodiment and the modified examples as a hydrogen sensor. This fuel-cell vehicle is a fuel-cell vehicle detecting a hydrogen gas in the vehicle using the hydrogen sensor.

Figure 13:
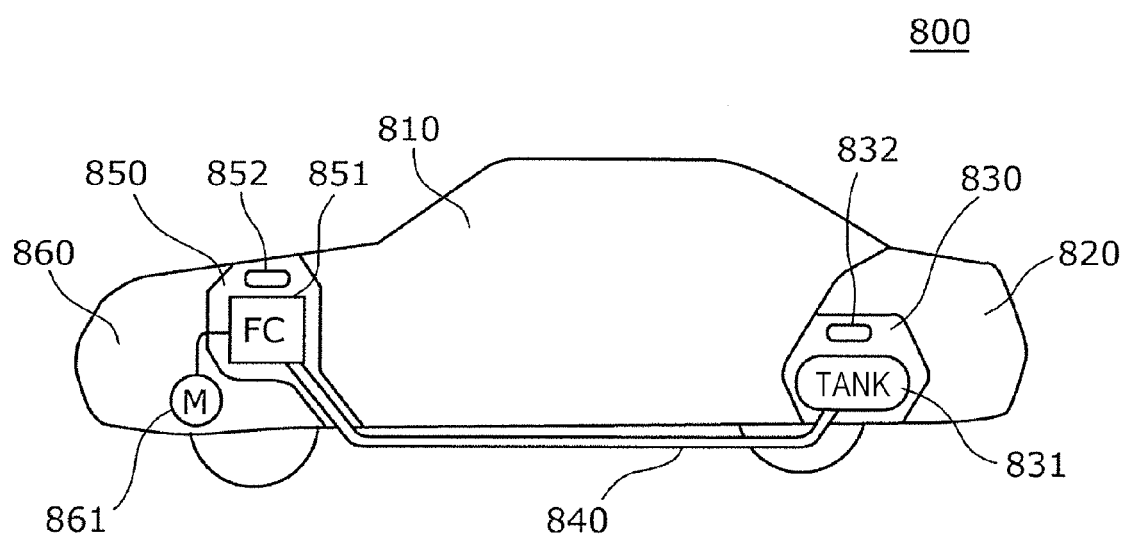
FIG. 13 is a side view showing a structural example of a fuel-cell vehicle according to a second embodiment.

FIG. 13 is a side view showing one structural example of a fuel-cell vehicle 800 according to the second embodiment.

The fuel-cell vehicle 800 includes a passenger compartment 810, a baggage room 820, a gas tank room 830, a fuel tank 831, a hydrogen sensor 832, a pipe arrangement 840, a fuel-cell room 850, a fuel cell 851, a hydrogen sensor 852, a motor room 860, and a motor 861.

The fuel tank 831 is provided in the gas tank room 830 and contains a hydrogen gas as a fuel gas. The hydrogen sensor 832 detects a fuel gas leakage in the gas tank room 830.

The fuel cell 851 is formed as a fuel-cell stack in which cells each including a fuel electrode, an air electrode, and an electrolyte as a basic unit are stacked to each other. This fuel cell 851 is provided in the fuel cell room 850. A hydrogen gas in the fuel tank 831 is supplied to the fuel cell 851 in the fuel-cell room 850 through the pipe arrangement 840. The fuel cell 851 generates an electrical power by a reaction between this hydrogen gas and an oxygen gas in the air. The hydrogen sensor 852 detects a hydrogen gas leakage in the fuel-cell room 850.

The motor 861 is provided in the motor room 860 and is rotated by an electrical power generated by the fuel cell 851, so that the fuel-cell vehicle 800 is driven.

As described above, in the gas sensor according to the present disclosure, as one example, by a very small power consumption of approximately 0.01 mW, a hydrogen gas can be detected. Hence, when the gas sensor is used for the hydrogen sensors 832 and 852, by excellent electrical power saving performance thereof, the hydrogen gas leakage can be always monitored without remarkably increasing a standby electrical power of the fuel-cell vehicle.

For example, regardless of the operation state of an ignition key of the fuel-cell vehicle 800, a predetermined voltage may be always applied to the hydrogen sensors 832 and 852. In this case, based on a current flowing through the hydrogen sensors 832 and 852, the presence or absence of a hydrogen gas outside the fuel tank 831 in the gas tank 830 and outside the fuel cell 851 in the fuel cell room 850 may be judged.

Accordingly, for example, when the ignition key is operated, since the presence or absence of a hydrogen gas leakage is already judged, compared to the case in which the presence or absence of a hydrogen gas leakage is judged after the ignition key is operated, the start-up time of a fuel-cell vehicle can be shortened. In addition, for example, even after the fuel-cell vehicle is driven and then stored in a garage, the safety can be improved by continuously monitoring a hydrogen gas leakage.

Overview of Embodiments

A gas sensor according to one aspect comprises a first conductive layer and a second conductive layer, the respective principal surfaces of which face each other; a metal oxide layer in contact with the principal surface of the first conductive layer and the principal surface of the second conductive layer; a local region which is disposed in the metal oxide layer so as to be in contact with the second conductive layer and which has a high degree of oxygen deficiency as compared to that of the metal oxide layer; and an insulation layer covering the first conductive layer, the second conductive layer, and the metal oxide layer. The other principal surface of the second conductive layer facing the above principal surface thereof is at least partially exposed without being covered with the insulation layer; the thickness of a first portion which is the exposed portion of the second conductive layer is smaller than the thickness of a second portion which is a portion of the second conductive layer covered with the insulation layer; and when the second conductive layer is in contact with a gas containing a gas molecule having a hydrogen atom, the resistance between the first conductive layer and the second conductive layer is decreased.

According to the structure as described above, a current flowing between the first conductive layer and the second conductive layer is concentrated in the local region having a high degree of oxygen deficiency. As a result, by a small current, the temperature of the local region can be increased. Hence, by the use of the self-heating and the gas sensitivity in the local region formed in the metal oxide layer, a hydrogen sensor excellent in electrical power saving can be obtained which is able to detect a hydrogen-containing gas without performing heating by a heater.

Since the local region is heated by a current flowing between the first conductive layer and the second conductive layer, at a portion of the second conductive layer in contact with the local region, a hydrogen atom is dissociated from the hydrogen-containing gas, and the hydrogen atom thus dissociated is bonded to an oxygen atom in the local region of the metal oxide layer, so that the resistance between the first conductive layer and the second conductive layer is decreased.

In more particular, when the temperature of the local region is increased, the temperature of the surface of the second conductive layer is also increased. In accordance with the increase in temperature, by the catalyst function of the second conductive layer, the efficiency of dissociation of a hydrogen atom from a gas molecule having a hydrogen atom at the second conductive layer is improved.

When a gas molecular having a hydrogen atom is brought into contact with the second conductive layer, a hydrogen atom is dissociated from the gas molecule, and the hydrogen atom thus dissociated diffuses in the second conductive layer and reaches the local region. In addition, the hydrogen atom is bonded to oxygen of a metal oxide present in the local region to form water ($H_2O$), and as a result, the degree of oxygen deficiency of the local region is further increased. Accordingly, a current is likely to flow in the local region, and the resistance between the first conductive layer and the second conductive layer is decreased.

Since the first portion having a thickness smaller than the thickness of the second portion is provided in the second conductive layer, the hydrogen atom dissociated from the hydrogen-containing gas at the first portion rapidly reaches the metal oxide layer. Accordingly, the resistance between the first conductive layer and the second conductive layer is rapidly decreased, and a hydrogen-containing gas can be rapidly detected.

In addition, the second conductive layer may be formed of a single layer in which the thickness of the first portion is different from that of the second portion.

According to the structure as described above, for example, by a relatively simple method in which after a flat plate having the thickness of the second conductive layer is formed, a part thereof is removed to form the first portion, the above second conductive layer is obtained.

In addition, the second conductive layer may be formed of an approximately flat-shaped first layer having the thickness of the first portion and a second layer provided on the first layer except for the first portion.

According to the structure as described above, for example, by a method in which after the first layer and the second layer are laminated to each other so as to have respective predetermined thicknesses, the second layer is selectively removed at the first portion, the second conductive layer in which the thickness of the first portion is accurately controlled can be obtained.

In addition, the gas sensor may further include a via which penetrates the insulation layer and is connected to the second portion of the second conductive layer.

According to the structure as described above, since the via is connected to the second portion having a thickness larger than that of the first portion of the second conductive layer, as compared to the case in which the via is connected to the first portion, the reliability of the electrical connection between the via and the second conductive layer is improved.

In addition, the metal oxide layer is formed by laminating a first metal oxide layer formed of a first metal oxide and a second metal oxide layer formed of a second metal oxide having a low degree of oxygen deficiency as compared to that of the first metal oxide; the first metal oxide layer is in contact with the first conductive layer, and the second metal oxide layer is in contact with the second conductive layer;

the local region is formed to penetrate at least the second metal oxide layer and to be in contact with the second conductive layer and may have a high degree of oxygen deficiency as compared to that of the second metal oxide layer.

According to the structure as described above, a laminate structure excellent in resistance change characteristic is used for the metal oxide layer, and hence, a gas sensor excellent in detection of a hydrogen-containing gas can be obtained.

In addition, the gas sensor may further include a third metal oxide layer which is formed along the periphery of the metal oxide layer and has a resistance higher than that of the metal oxide layer.

According to the structure as described above, the position at which the local region is to be formed can be controlled at a position in the metal oxide layer except for the third metal oxide layer at which a preferable detection performance of a hydrogen-containing gas can be obtained.

In addition, the local region may be present right under the first portion of the second conductive layer.

According to the structure as described above, since the local region is formed at a position at which a hydrogen atom dissociated from the hydrogen-containing gas at the first portion is likely to reach, a hydrogen sensor excellent in detection of a hydrogen-containing gas can be obtained.

In addition, the second conductive layer may be formed of a material having a catalyst function of dissociating the hydrogen atom from the gas molecule.

According to the structure as described above, at a portion of the second conductive layer in contact with the local region, a hydrogen atom is dissociated from the hydrogen-containing gas, and the hydrogen atom thus dissociated is bonded to an oxygen atom in the local region of the metal oxide layer, so that the resistance between the first conductive layer and the second conductive layer is decreased.

In addition, the second conductive layer may contain platinum or palladium.

According to the structure as described above, the second conductive layer can dissociate a hydrogen atom from the hydrogen molecule by the catalyst function of platinum or palladium.

In addition, the metal oxide layer may be reversibly changed between a high resistive state and a low resistive state in accordance with the voltage to be applied between the first conductive layer and the second conductive layer.

According to the structure as described above, the resistive state of the metal oxide layer can also be changed besides the change caused by a hydrogen gas. For example, after the metal oxide layer is set in a high resistive state, a gas to be inspected may be brought into contact with the metal oxide layer. Accordingly, the decrease in resistance can be clearly detected, and hence, the detection performance of a hydrogen-containing gas is improved.

In addition, the gas sensor may further include a measurement circuit measuring a current flowing in the metal oxide layer when a predetermined voltage is applied between the first conductive layer and the second conductive layer. In addition, the gas sensor may further include an electrical power source which always applies a predetermined voltage between the first conductive layer and the second conductive layer.

According to the structure as described above, as a module component including a measurement circuit and an electrical power source, a highly convenient hydrogen sensor can be obtained. In particular, by excellent electrical power saving of the above hydrogen sensor, a hydrogen gas leakage can be continuously monitored with a small electrical power.

In addition, the first metal oxide and the second metal oxide each may be either a transition metal oxide or an aluminum oxide.

According to the structure as described above, since a transition metal oxide or an aluminum oxide, each of which is excellent in resistance change characteristic, is used as the first metal oxide and the second metal oxide, a hydrogen sensor excellent in detection of a hydrogen-containing gas can be obtained.

In addition, the first metal oxide and the second metal oxide may be oxides formed of the same transition metal.

According to the structure as described above, since a common material is used for the first metal oxide and the second metal oxide, a gas sensor formable by a simpler manufacturing method can be obtained.

In addition, the first metal oxide and the second metal oxide may be oxides formed of transition metals different from each other.

According to the structure as described above, since the range of material selection of the first meta oxide and the second metal oxide is increased, a hydrogen sensor excellent in detection of a hydrogen-containing gas can be obtained.

In addition, the transition metal oxide may be a tantalum oxide, a hafnium oxide, or a zirconium oxide.

According to the structure as described above, since a tantalum oxide, a hafnium oxide, or a zirconium oxide, each of which is excellent in resistance change characteristic, is used as the transition metal oxide described above, a hydrogen sensor excellent in detection of a hydrogen-containing gas can be obtained.

In addition, since the local region is heated by a current flowing between the first conductive layer and the second conductive layer, a hydrogen atom is dissociated from the gas molecule at an exposed portion of the second conductive layer, and the hydrogen atom thus dissociated is bonded to an oxygen atom in the local region of the metal oxide layer, so that the resistance of the metal oxide layer may be decreased.

According to the structure as described above, the current flowing between the first conductive layer and the second conductive layer is concentrated in the local region having a high degree of oxygen deficiency. As a result, by a small current, the temperature of the local region can be increased. Accordingly, by the use of the self-heating and the gas sensitivity in the local region formed in the metal oxide layer, a gas sensor excellent in electrical power saving can be obtained which can detect a hydrogen-containing gas without performing heating by a heater.

A hydrogen detection method according to one aspect is a hydrogen detection method using a gas sensor which comprises: a first conductive layer and a second conductive layer, the respective principal surfaces of which face each other; a metal oxide layer disposed so as to be in contact with the principal surface of the first conductive layer and in contact with the principal surface of the second conductive layer; a local region disposed in the metal oxide layer in contact with the second conductive layer and having a high degree of oxygen deficiency as compared to that of the metal oxide layer: and an insulation layer covering the first conductive layer, the second conductive layer, and the metal oxide layer. The other principal surface of the second conductive layer facing the above principal surface thereof is at least partially exposed without being covered with the insulation layer; the thickness of a first portion which is the exposed portion of the second conductive layer is smaller than the thickness of a second portion which is a portion of the second conductive layer covered with the insulation layer; and in the hydrogen detection method, when a gas to be inspected is brought into contact with the first portion of the second conductive layer, the resistance between the first conductive layer and the second conductive layer is decreased, so that a gas having a hydrogen atom contained in the gas to be inspected is detected.

According to the method as described above, by the use of the self-heating and the gas sensitivity in the local region formed in the metal oxide layer, since a hydrogen-containing gas can be detected without performing heating by a heater, hydrogen detection excellent in electrical power saving can be performed. In addition, since the second conductive layer includes the first portion having a smaller thickness than that of the second portion, a hydrogen atom dissociated from a hydrogen-containing gas brought into contact with the first portion rapidly reaches the metal oxide layer. As a result, the resistance between the first conductive layer and the second conductive layer is rapidly decreased, and a hydrogen-containing gas can be rapidly detected.

A fuel-cell vehicle according to one aspect is a fuel-cell vehicle in which the gas sensor described above is disposed in at least one of a gas tank room in which a hydrogen gas tank is disposed and a fuel-cell room in which a fuel cell is disposed.

According to the structure as described above, by excellent electrical power saving of the hydrogen sensor, without remarkably increasing a standby electrical power of the fuel-cell vehicle, a fuel gas leakage can be always monitored.

For example, when an ignition key is operated, since the presence or absence of a fuel gas leakage is already judged, compared to the case in which after an ignition key is operated, a hydrogen sensor is driven in order to judge the presence or absence of a fuel gas leak, the start-up time of a fuel-cell vehicle can be shortened. In addition, for example, even after the fuel-cell vehicle is driven and then stored in a garage, the safety can be improved by continuously monitoring a hydrogen gas leakage.

A hydrogen detection method according to one aspect is a method to judge whether a hydrogen gas is present or absent in at least one of the outside of the tank in the gas tank room and the outside of the fuel cell in the fuel-cell room by always applying a predetermined voltage to the gas sensor in the fuel-cell vehicle.

According to the structure as described above, by excellent electrical power saving of the gas sensor, without remarkably increasing a standby electrical power of the fuel-cell vehicle, a fuel gas leakage can be continuously monitored.

For example, when an ignition key is operated, since the presence or absence of a fuel gas leakage is already judged, compared to the case in which after an ignition key is operated, a hydrogen sensor is driven in order to judge the presence or absence of a fuel gas leak, the start-up time of a fuel-cell vehicle can be shortened. In addition, for example, even after the fuel-cell vehicle is driven and then stored in a garage, since a fuel gas leakage is continuously monitored, the safety can be improved.

The gas sensor according to the present disclosure may be applied, for example, to a fuel-cell vehicle, a hydrogen station, and a hydrogen plant.

What is claimed is:

1. A hydrogen detection method using a gas sensor, wherein the gas sensor includes:
    a first conductive layer;
    a second conductive layer including a first region having a first thickness and a second region having a second thickness larger than the first thickness;
    a metal oxide layer disposed between the first conductive layer and the second conductive layer, the metal oxide layer including a bulk region and a local region surrounded by the bulk region, a degree of oxygen deficiency of the local region being higher than that of the bulk region; and
    an insulation layer covering the first conductive layer, the second region of the second conductive layer, and the metal oxide layer and not covering the first region of the second conductive layer,
the hydrogen detection method comprising:
    allowing a gas to come into contact with the first region of the second conductive layer; and
    detecting a hydrogen gas contained in the gas by detecting a decrease in resistance between the first conductive layer and the second conductive layer,
wherein the first thickness and the second thickness are in a direction perpendicular to a stacking direction between the second conductive layer and the metal oxide layer.

* * * * *